(12) United States Patent
Barrett et al.

(10) Patent No.: US 9,285,305 B2
(45) Date of Patent: Mar. 15, 2016

(54) SHROUDED SENSOR CLIP ASSEMBLY AND BLOOD CHAMBER FOR AN OPTICAL BLOOD MONITORING SYSTEM

(71) Applicant: Fresenius Medical Care Holdings, Inc., Waltham, MA (US)

(72) Inventors: Louis L. Barrett, West Point, UT (US); Perry N. Law, Centerville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/263,570

(22) Filed: Apr. 28, 2014

(65) Prior Publication Data

US 2014/0233026 A1    Aug. 21, 2014

Related U.S. Application Data

(63) Continuation of application No. 13/405,148, filed on Feb. 24, 2012, now Pat. No. 8,743,354, which is a continuation-in-part of application No. 13/034,788, filed on Feb. 25, 2011, now Pat. No. 8,517,968, and a (Continued)

(51) Int. Cl.
  *G01N 21/05*  (2006.01)
  *A61B 5/145*  (2006.01)
  (Continued)

(52) U.S. Cl.
  CPC .............. *G01N 21/05* (2013.01); *A61B 5/1455* (2013.01); *A61B 5/14557* (2013.01);
  (Continued)

(58) Field of Classification Search
  None
  See application file for complete search history.

(56) References Cited

U.S. PATENT DOCUMENTS

| 2,357,238 | A | 8/1944 | Trimble |
| D206,714 | S | 1/1967 | Badkar |

(Continued)

FOREIGN PATENT DOCUMENTS

| CN | 101015455 A | 8/2007 |
| CN | 101113477 A | 1/2008 |

(Continued)

OTHER PUBLICATIONS

Official Action for European Patent Application No. 11801888.6, dated Apr. 9, 2015.

(Continued)

*Primary Examiner* — Gordon J Stock, Jr.
(74) *Attorney, Agent, or Firm* — Leydig, Voit & Mayer, Ltd.

(57) ABSTRACT

An optical blood monitoring system for blocking unwanted light from reaching sensors in a sensor clip assembly fastened to a blood chamber connected in an extracorporeal blood treatment system. The blood chamber has an internal flow cavity for communicating the extracorporeal blood flow and viewing windows to enable the sensor clip assembly to illuminate the blood with light as the blood flows through the blood chamber in order to monitor characteristics of the blood. The sensor clip assembly includes opposing heads with LED emitters and photodetectors. In one embodiment, lenses in the heads are surrounded by shrouds extending from the lenses so that when the sensor clip assembly is fastened to the blood chamber the shrouds block unwanted light from reaching the photodetectors. Either alternatively or as a complement to the shrouds, the blood chamber includes an opaque portion or a portion colored to attenuate particular wavelengths of light to further enhance the overall ability of the blood chamber and sensor clip assembly to block unwanted light from reaching the photodetectors.

16 Claims, 35 Drawing Sheets

Related U.S. Application Data continuation-in-part of application No. 12/876,572, filed on Sep. 7, 2010, now Pat. No. 9,194,792, and a continuation-in-part of application No. 12/876,798, filed on Sep. 7, 2010, now Pat. No. 8,333,724.

(60) Provisional application No. 61/553,078, filed on Oct. 28, 2011.

(51) Int. Cl.
  *A61B 5/1455* (2006.01)
  *A61M 1/36* (2006.01)
  *G01N 33/49* (2006.01)

(52) U.S. Cl.
  CPC .............. *A61M 1/367* (2013.01); *G01N 33/49* (2013.01); *A61B 5/14535* (2013.01); *A61B 2562/185* (2013.01); *A61M 2205/3306* (2013.01); *A61M 2205/3313* (2013.01); *A61M 2230/205* (2013.01); *A61M 2230/207* (2013.01)

(56) References Cited

U.S. PATENT DOCUMENTS

| | | |
|---|---|---|
| D212,218 S | 9/1968 | Norton |
| 3,507,951 A | 4/1970 | Baily |
| 3,580,683 A | 5/1971 | Schulkind |
| 3,728,032 A | 4/1973 | Noll |
| 3,740,156 A | 6/1973 | Heigl et al. |
| 4,243,883 A | 1/1981 | Schwarzmann |
| 4,371,498 A * | 2/1983 | Scordato .............. G01N 21/03 356/246 |
| D270,281 S | 8/1983 | Andersen et al. |
| 4,444,498 A | 4/1984 | Heinemann |
| 4,784,768 A | 11/1988 | Mathieu |
| 4,936,993 A | 6/1990 | Nomura |
| 5,073,171 A | 12/1991 | Eaton |
| 5,171,456 A | 12/1992 | Hwang et al. |
| D335,096 S | 4/1993 | Marsch |
| 5,222,948 A | 6/1993 | Austin et al. |
| 5,231,464 A | 7/1993 | Ichimura et al. |
| 5,247,434 A | 9/1993 | Peterson et al. |
| 5,312,535 A | 5/1994 | Waska et al. |
| 5,351,686 A | 10/1994 | Steuer et al. |
| 5,366,630 A | 11/1994 | Chevallet |
| 5,372,136 A | 12/1994 | Steuer et al. |
| 5,456,253 A | 10/1995 | Steuer et al. |
| 5,458,566 A | 10/1995 | Herrig et al. |
| 5,476,764 A | 12/1995 | Bitensky |
| 5,670,050 A | 9/1997 | Brose et al. |
| 5,674,390 A | 10/1997 | Matthews et al. |
| 5,676,644 A | 10/1997 | Toavs et al. |
| 5,729,333 A | 3/1998 | Osten et al. |
| 5,730,712 A | 3/1998 | Falkvall et al. |
| 5,762,805 A | 6/1998 | Truitt et al. |
| 5,769,815 A | 6/1998 | Utterberg |
| 5,779,529 A | 7/1998 | Bizer |
| 5,792,052 A | 8/1998 | Isaacson et al. |
| D409,750 S | 5/1999 | Hacker |
| 6,018,673 A | 1/2000 | Chin et al. |
| 6,069,687 A | 5/2000 | Briggs |
| 6,090,061 A | 7/2000 | Steuer et al. |
| 6,284,131 B1 | 9/2001 | Hogard et al. |
| 6,284,142 B1 | 9/2001 | Muller |
| 6,510,330 B1 | 1/2003 | Enejder |
| 6,554,788 B1 | 4/2003 | Hunley et al. |
| 6,746,415 B1 | 6/2004 | Steuer et al. |
| 6,784,820 B1 | 8/2004 | Casalegno et al. |
| 7,018,353 B2 | 3/2006 | Hunley et al. |
| D518,573 S | 4/2006 | French |
| 7,241,825 B2 | 7/2007 | Koga et al. |
| 7,247,143 B2 | 7/2007 | Law et al. |
| 7,671,974 B2 | 3/2010 | O'Mahoney et al. |
| D623,302 S | 9/2010 | Barrett et al. |
| D625,824 S | 10/2010 | Brackett et al. |
| D630,536 S | 1/2011 | Pettit |
| D654,999 S | 2/2012 | Barrett et al. |
| 8,133,194 B2 | 3/2012 | Szamosfalvi et al. |
| 8,287,739 B2 | 10/2012 | Barrett et al. |
| 8,315,682 B2 | 11/2012 | Such et al. |
| 8,328,748 B2 | 12/2012 | Law et al. |
| 8,333,724 B2 | 12/2012 | Barrett et al. |
| D684,695 S | 6/2013 | Green et al. |
| D684,697 S | 6/2013 | Green et al. |
| 8,517,968 B2 | 8/2013 | Barrett et al. |
| D698,440 S | 1/2014 | Lombardi et al. |
| 9,002,655 B2 | 4/2015 | Bene |
| 2001/0016699 A1 | 8/2001 | Burbank et al. |
| 2001/0021817 A1 | 9/2001 | Brugger et al. |
| 2001/0037079 A1 | 11/2001 | Burbank et al. |
| 2001/0041892 A1 | 11/2001 | Burbank et al. |
| 2002/0103453 A1 | 8/2002 | Burbank et al. |
| 2002/0147423 A1 | 10/2002 | Burbank et al. |
| 2003/0009123 A1 | 1/2003 | Brugger et al. |
| 2003/0045784 A1 | 3/2003 | Palatnik et al. |
| 2003/0070969 A1 | 4/2003 | Muller et al. |
| 2003/0097087 A1 | 5/2003 | Gura |
| 2003/0143116 A1 | 7/2003 | Zheng et al. |
| 2003/0196949 A1 | 10/2003 | Sunohara et al. |
| 2003/0210390 A1 | 11/2003 | O'Mahoney et al. |
| 2003/0212316 A1 | 11/2003 | Leiden et al. |
| 2004/0087845 A1 | 5/2004 | Katarow et al. |
| 2005/0094127 A1 | 5/2005 | O'Mahony et al. |
| 2006/0036185 A1 | 2/2006 | Lewicke et al. |
| 2006/0144776 A1 | 7/2006 | Mishkin et al. |
| 2006/0226079 A1 | 10/2006 | Mori et al. |
| 2006/0290625 A1 | 12/2006 | Sugimoto |
| 2007/0015963 A1 | 1/2007 | Fengler et al. |
| 2007/0100219 A1 | 5/2007 | Sweutzer et al. |
| 2007/0149871 A1 | 6/2007 | Sarussi et al. |
| 2007/0179433 A1 | 8/2007 | Jonsson et al. |
| 2008/0081970 A1 | 4/2008 | Boyce et al. |
| 2008/0129047 A1 | 6/2008 | Blivet et al. |
| 2008/0300570 A1 | 12/2008 | Fowles et al. |
| 2009/0054751 A1 | 2/2009 | Babashan et al. |
| 2009/0247850 A1 | 10/2009 | Porges |
| 2010/0004518 A1 | 1/2010 | Vo et al. |
| 2010/0110416 A1* | 5/2010 | Barrett et al. .................. 356/40 |
| 2010/0113891 A1 | 5/2010 | Barrett et al. |
| 2010/0168531 A1 | 7/2010 | Shaltis et al. |
| 2011/0004082 A1 | 1/2011 | Poeze et al. |
| 2011/0022077 A1 | 1/2011 | Green et al. |
| 2011/0160679 A1 | 6/2011 | Okiyama et al. |
| 2012/0120384 A1 | 5/2012 | Barrett et al. |
| 2012/0154789 A1 | 6/2012 | Barrett et al. |

FOREIGN PATENT DOCUMENTS

| | | |
|---|---|---|
| EP | 0 274 178 A1 | 7/1988 |
| EP | 467805 A1 | 1/1992 |
| EP | 0 990 444 A2 | 4/2000 |
| GB | 1 583 023 A | 1/1981 |
| JP | 56031085 A | 3/1981 |
| JP | H03-127990 U | 12/1991 |
| JP | 09-229847 | 9/1997 |
| JP | 2006199845 A | 8/2006 |
| JP | 2009-216711 | 9/2009 |
| WO | WO 93/06456 | 4/1993 |
| WO | WO 93/06774 A1 | 4/1993 |
| WO | 00/33053 A1 | 6/2000 |
| WO | WO 01/93944 A1 | 12/2001 |
| WO | WO 02/078783 A2 | 10/2002 |

OTHER PUBLICATIONS

Office action for Chinese Patent Application No. 201280010099.2, dated Apr. 22, 2015.
International Search Report and Written Opinion for related International No. PCT/US2012/026637 dated Jun. 6, 2012.
Sacker-Berstein, Jonathan D., M.D., et al., "*How Should Diuretic-Refractory Volume-Overloaded Heart Failure Patients Be Managed?*", The Journal of Invasive Cardiology, vol. 15., No. 10 (Oct. 2003), pp. 585-590, retrieved from http://www.medscape.com/viewarticle/463509_print on Mar. 11, 2013, pp. 1-11.

(56) References Cited

OTHER PUBLICATIONS

Jaski, Brian E., M.D., "*Peripherally Inserted Veno-Venous Ultrafiltration for Rapid Treatment of Volume Overloaded Patients*", *Journal of Cardiac Failure*, vol. 9, No. 3 (Jun. 2003) pp. 227-231.
Blood Chamber 2001—Admitted Prior Art.
CL Photo 2000—Admitted Prior Art.
Blood Chamber Instruction Sheet 2001—Admitted Prior Art.
Office action for co-pending Canadian Patent Application No. 2,742,619, dated Aug. 5, 2013.
Original claims as filed for co-pending Canadian Patent Application No. 2,742,619 including a Voluntary Amendment dated Sep. 6, 2011.
Office action for co-pending Canadian Patent Application No. 2,742,794, including original claims as filed, Apr. 2013.
Official action for co-pending European Patent Application No. 11 755 533.4 dated Apr. 16, 2013.
Official action for co-pending European Patent Application No. 11 754 974.1 dated Apr. 16, 2013.
Official Action from co-pending Canadian Patent Application No. 2,742,619, dated Nov. 6, 2014 (5 pages).
Japanese Office action for Japanese Patent Application No. 58245/2013, dated Dec. 24, 2014, (5 pages).
Chinese Office action for Chinese Patent Application No. 201180042991.4, dated Jan. 19, 2015, (9 pages).
Examination Report for Australian Patent No. 2012222113 dated Aug. 5, 2015,(3 pages).
Chinese Office Action for Chinese Patent Application No. 201180055375.2, dated Mar. 16, 2015 (43 pages total).
Third Office action of related Chinese Patent Application No. 201180042991.4, dated Jul. 31, 2015.
Japanese Patent Application No. 555623/2013, Office Action (Dec. 22, 2015).

\* cited by examiner

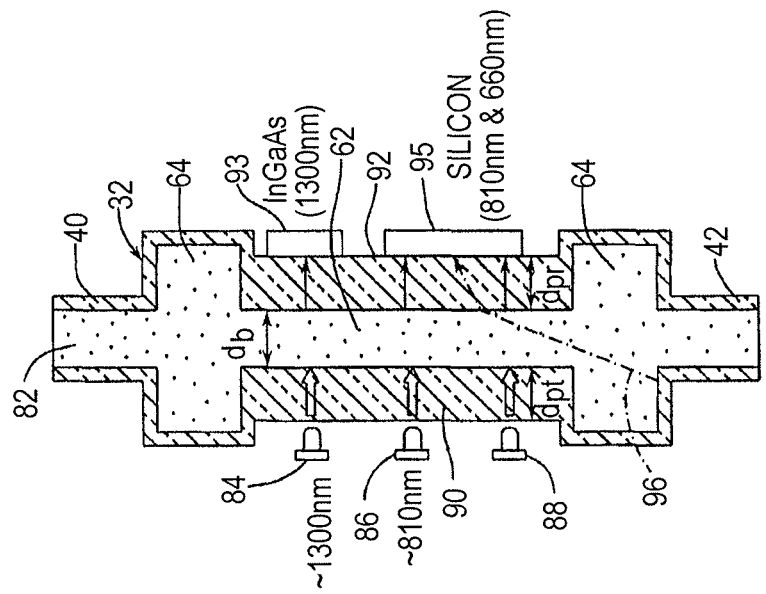
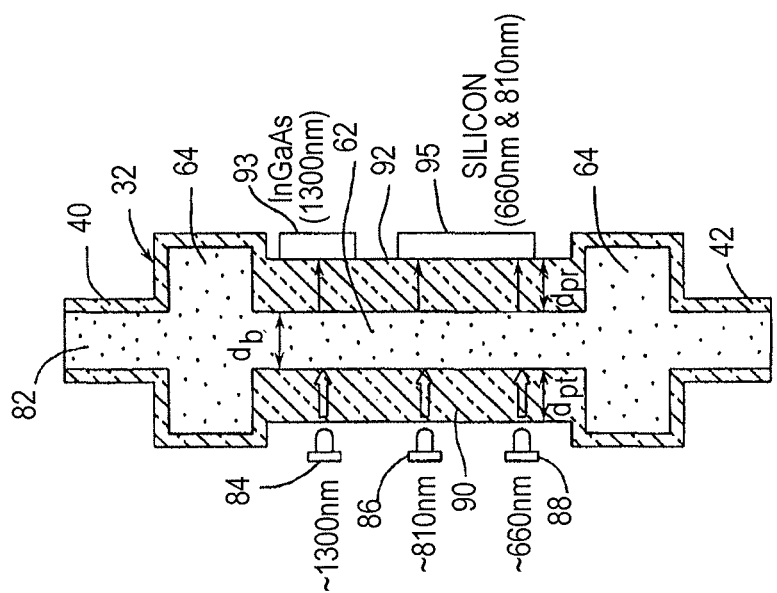
FIG. 5A
FIG. 5B

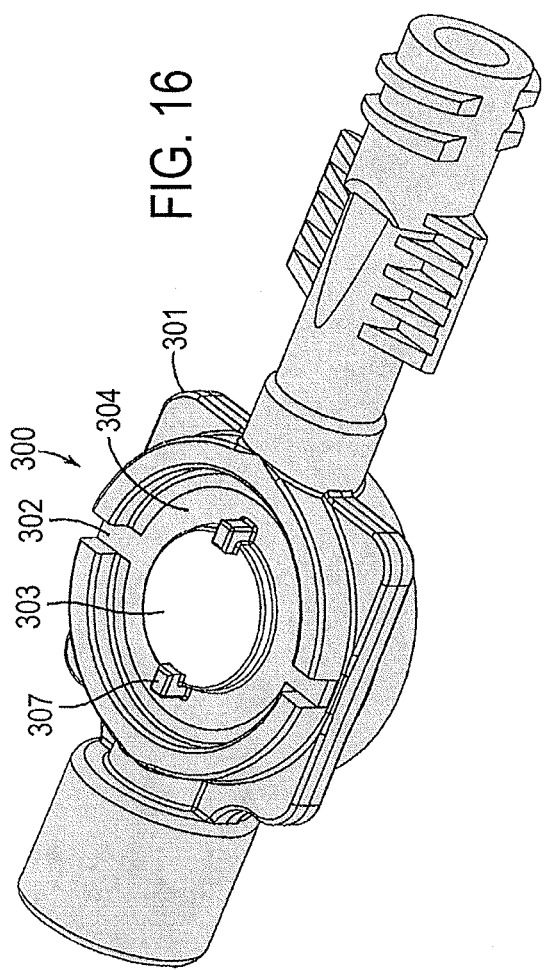
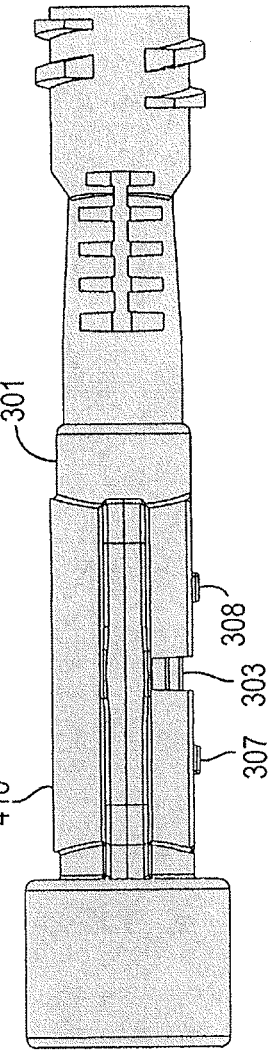

SHROUDED SENSOR CLIP ASSEMBLY AND BLOOD CHAMBER FOR AN OPTICAL BLOOD MONITORING SYSTEM

RELATED APPLICATIONS

This application is a continuation of U.S. application Ser. No. 13/405,148, filed Feb. 24, 2012, which claims priority to U.S. Provisional Application No. 61/553,078, filed Oct. 28, 2011. U.S. application Ser. No. 13/405,148 is also a continuation-in-part of U.S. application Ser. No. 13/034,788, filed Feb. 25, 2011; Ser. No. 12/876,798, filed Sep. 7, 2010; and Ser. No. 12/876,572, filed Sep. 7, 2010. The disclosures of all of these applications are incorporated herein by reference in their entireties.

TECHNICAL FIELD

The disclosure generally relates to optical blood monitoring systems used to monitor extracorporeal patient blood flow and take real-time measurement of hematocrit, oxygen saturation levels and/or other blood constituents. The disclosure more particularly is directed to improving the noise immunity of such systems.

BACKGROUND

Patients with kidney failure or partial kidney failure typically undergo hemodialysis treatment in order to remove toxins and excess fluids from their blood. To do this, blood is taken from a patient through an intake needle or catheter which draws blood from an artery or vein located in a specifically accepted access location—e.g., a shunt surgically placed in an arm, thigh, subclavian and the like. The needle or catheter is connected to extracorporeal tubing that is fed to a peristaltic pump and then to a dialyzer that cleans the blood and removes excess fluid. The cleaned blood is then returned to the patient through additional extracorporeal tubing and another needle or catheter. Sometimes, a heparin drip is located in the hemodialysis loop to prevent the blood from coagulating.

As the drawn blood passes through the dialyzer, it travels in straw-like tubes within the dialyzer that serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste. The red cells remain in the straw-like tubes and their volume count is unaffected by the process.

A blood monitoring system is often used during hemodialysis treatment or other treatments involving extracorporeal blood flow. One example is the CRIT-LINE® monitoring system sold by Fresenius USA Manufacturing, Inc. of Waltham, Mass. The CRIT-LINE® blood monitoring system uses optical techniques to non-invasively measure in real-time the hematocrit and the oxygen saturation level of blood flowing through the hemodialysis system. The blood monitoring system measures the blood at a sterile blood chamber attached in-line to the extracorporeal tubing, typically on the arterial side of the dialyzer.

In general, blood chambers along with the tube set and dialyzer are replaced for each patient. The blood chamber is intended for a single use. The blood chamber defines an internal blood flow cavity comprising a substantially flat viewing region and two opposing viewing lenses. LED emitters and photodetectors for the optical blood monitor are clipped into place onto the blood chamber over the lenses. Multiple wavelengths of light may be directed through the blood chamber and the patient's blood flowing through the chamber with a photodetector detecting the resulting intensity of each wavelength.

The preferred wavelengths to measure hematocrit are about 810 nm, which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System and Method for Non-Invasive Hematocrit Monitoring," which issued on Dec. 13, 1999 and is assigned to the assignee of the present application, uses this light intensity information to calculate the patient's hematocrit value in real-time. The hematocrit value, as is widely used in the art, is a percentage determined by the ratio between (1) the volume of the red blood cells in a given whole blood sample and (2) the overall volume of the blood sample.

In a clinical setting, the actual percentage change in blood volume occurring during hemodialysis can be determined, in real-time, from the change in the measured hematocrit. Thus, an optical blood monitor is able to non-invasively monitor not only the patient's hematocrit level but also the change in the patient's blood volume in real-time during a hemodialysis treatment session. The ability to monitor real-time change in blood volume helps facilitate safe, effective hemodialysis.

To monitor blood in real time, light emitting diodes (LEDs) and photodetectors for them are mounted on two opposing heads of a sensor clip assembly that fit over the blood chamber. For accuracy of the system, it is important that the LEDs and the photodetectors be located in a predetermined position and orientation each time the sensor clip assembly is clipped into place over the blood chamber. The predetermined position and orientation ensures that light traveling from the LEDs to the photodetectors travels through a lens of the blood chamber.

The optical monitor is calibrated for the specific dimensions of the blood chamber and the specific position and orientation of the sensor clip assembly with respect to the blood chamber. For this purpose, the heads of the sensor clips are designed to mate to the blood chamber so that the LEDs and the photodetectors are at a known position and orientation. In the CRIT-LINE® monitoring system, the head of the sensor clips and the blood chamber have complementary D-shaped configurations.

Under certain conditions, unwanted light can mix with the light traveling directly from the LEDs, through the blood in the chamber and into the photodetectors, causing inaccuracies in the measured hematocrit and/or oxygen saturation levels. Signal processing techniques remedy most of the issues pertaining to ambient light under most conditions. In addition, the blood chambers may include a "moat" around the lens area, which allows blood to flow around the area of the lens as well as through it. This moat fills with blood and under most conditions effectively blocks unwanted light from reaching the photodetectors on the sensor clip assembly. The effectiveness of the moat depends on many factors including the condition of the patient's blood and the wavelength spectrum of the unwanted light. For example, when a patient displays very low hematocrit values, the ability of the moat to effectively block unwanted light is compromised, allowing greater amounts of noise to enter into the signal measured by the photodetectors.

SUMMARY

A primary objective of the disclosure is to facilitate the accurate measurement of hematocrit and oxygen saturation levels over the expected full dynamic range of their values, and to particularly maintain highly accurate values when the blood being measured is characterized by low hematocrit levels.

In one aspect of the disclosure, a body of a blood chamber is at least partially made of material opaque to a wavelength region of a light beam associated with the blood chamber to calculate oxygen saturation levels of blood flowing through the blood chamber, thereby attenuating unwanted light (noise) and effectively preventing it from mixing with the measurement light beam. Attenuating unwanted light (e.g., light ducting through the chamber body) increases the range of accurate measurement of oxygen saturation levels and particularly improves the accuracy of the measurements at low levels of oxygen saturation that commonly are present when patients have low hematocrit values.

To further protect against the injection of noise into the measurement light beam, another aspect of the disclosure shrouds photoemitters and photodetectors that create and detect the light beam in order to prevent ambient light from strongly mixing with the measurement beam. The shroud is an integral part of either the blood chamber and/or a sensor clip assembly that generates and detects the light beam. In the illustrated embodiment, the shroud is part of the sensor clip assembly and a free end of each shroud is received by an annular receptacle in the blood chamber. But the shroud may alternatively be part of the blood chamber and the receptacle part of the clip. Either way, each shroud encircles and extends between a window of the blood chamber and a lens of the photoemitters or the photodetectors. By extending each shroud beyond the lens in the head of the sensor clip assembly, the shroud effectively isolates optical noise sourcing from both ambient light and indirect light from the photoemitters resulting from ducting of the photoemitters' light by areas of the chamber outside of the window.

Another aspect of the disclosure enables the shrouds to fasten the sensor clip assembly to the blood chamber, thereby providing an optically robust and mechanically secure interface between the chamber and clip. To fasten the clip and blood chamber, the illustrated embodiment includes a spring in the clip so the blood chamber is gripped between the two heads of the clip. When mated with the shrouds, annular receptacles in the blood chamber align the photoemitters and the photodetectors with the windows of the blood chamber. To prevent relative rotation between them, the interface between the clip and the chamber includes a mechanical stop. In the illustrated embodiment, the blood chamber includes one or more anti-rotation tabs that are received by complementary anti-rotation slots in the housing to prevent relative rotation. The anti-rotation tabs and mating, complementary slots may take on any reasonable geometric shape. Furthermore, other types of fasteners or rotational stops may work equally well and are contemplated. For example, either the blood chamber or the clip can include alignment posts that guide the blood chamber and clip into proper engagement to both register the LEDs and photodetectors with the lenses and prevent rotation.

Other advantages and features of the disclosure may be apparent to those skilled in the art upon reviewing the drawings and the following description thereof.

BRIEF DESCRIPTION OF THE DRAWINGS

FIG. 5A is a schematic drawing illustrating the detection of light and infrared light at various wavelengths through the blood chamber in order to monitor the hematocrit and oxygen saturation of the blood passing through the blood chamber.

FIG. 5B is a schematic drawing similar to FIG. 5A further illustrating the effect of ambient or ducted light that does not pass through the direct path through the blood in the blood flow chamber.

FIG. 16 is a perspective view of the other side of the blood chamber shown in FIG. 15.

FIG. 17 is a front elevation view of the blood chamber shown in FIG. 15.

DETAILED DESCRIPTION

Figure 1:
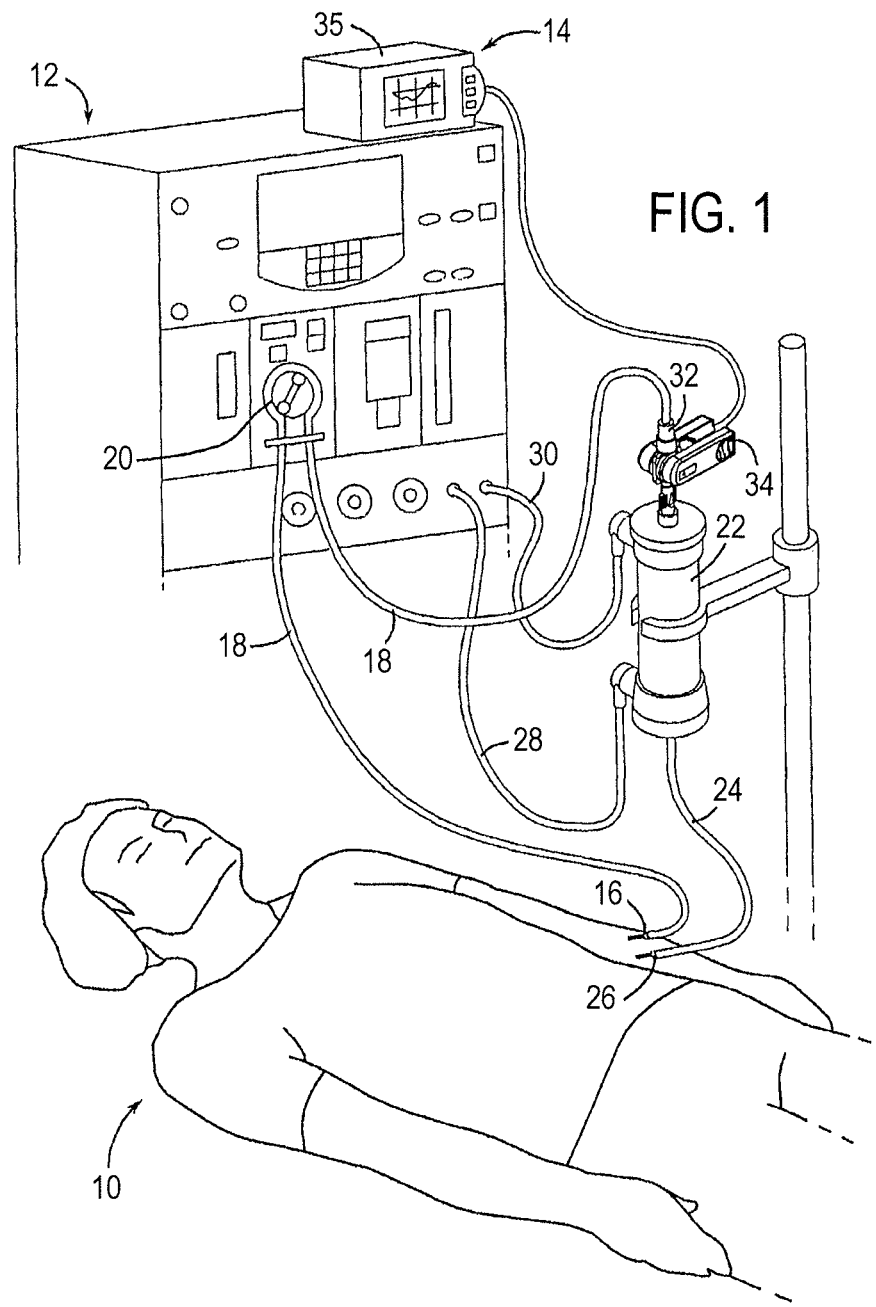
FIG. 1 is a perspective view of a patient undergoing hemodialysis treatment with a non-invasive, optical blood monitor monitoring the patient's blood in real-time as it passes through extracorporeal tubing in the hemodialysis system utilizing a conventional blood chamber and sensor clip assembly.

FIG. 1 illustrates a patient 10 undergoing hemodialysis treatment with a conventional hemodialysis system 12, and also illustrates a non-invasive, optical blood monitor 14. A typical hemodialysis clinic will have several hemodialysis systems 12 for treating patients.

An input needle or catheter 16 is inserted into an access site of the patient 10, such as shunt in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer 22 to the patient through extracorporeal tubing 24 and a return needle or catheter 26. The extracorporeal blood flow in the United States generally receives a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours. In a typical hemodialysis treatment as described in FIG. 1, the access site draws arterial blood from the patient. If no arterial access is available then a venous catheter may be used to access the patient's blood. As mentioned, other dialysis applications such as low flow Continuous Renal Replacement Therapy (CRRT) sometimes used in the Intensive Care Unit and high-flow perfusion measurements during cardiac surgery also measure blood from the patient. Current art indicates that oxygen saturation levels in venous blood correlate to the cardiac output for the patient. The typical blood monitor 14 shown in FIG. 1 can be used in these other applications as well.

The optical blood monitor 14 includes a blood chamber 32, a sensor clip assembly 34, and a controller 35. The blood chamber 32 is typically located in line with the extracorporeal tubing 18 upstream of the dialyzer 22. Blood from the peristaltic pump 20 flows through the tubing 18 into the blood chamber 32. The preferred sensor assembly 34 includes LED photoemitters that emit light at substantially 810 nm, which is isobestic for red blood cells, substantially 1300 nm, which is isobestic for water, and at substantially 660 nm, which is sensitive for oxygenated hemoglobin. The blood chamber 32 includes windows so that the sensor emitters and detector(s) can view the blood flowing through the blood chamber 32, and determine the patient's real-time hematocrit value and oxygen saturation value using known ratiometric techniques.

Referring now to FIGS. 2A-4B, the body of a conventional blood chamber 32 is made of molded, medical grade, clear polycarbonate. It includes a raised, stepped rim 33 having a double-D configuration. It also includes two viewing windows 36, 38 (see FIG. 4A). In the illustrated embodiments described hereinafter, the inlet 40 and outlet 42 of the blood chamber are designed to be compatible with standard medical industry connecting devices, conventionally known as Luer lock connectors. Alternatively, one or both of the inlet 40 and outlet 42 may be configured to include an opening that accepts the outer circumference of the tubing 30.

In the blood chamber 32 shown in FIGS. 2A-4B, the inlet 40 is integrally molded with the blood chamber 32, whereas the outlet 42 consists of a suitable off-the-shelf connection adapter bonded to the body of the blood chamber 32. The adapter is preferably a non-latex and non-phthalate material such as AM287T tri-octyl-trimellithate. Bonding of the adapter to provide the outlet 42 is accomplished using a mixed solvent cocktail of 50% methyl ethyl ketone and 50% Cyclohexanone. Bonding the adapter to the body of the blood chamber must be done carefully to avoid getting the solvent in the cavity of the blood chamber. Exposure of the internal cavity of the blood chamber to the solvent will crack the body of the chamber.

Figure 2A:
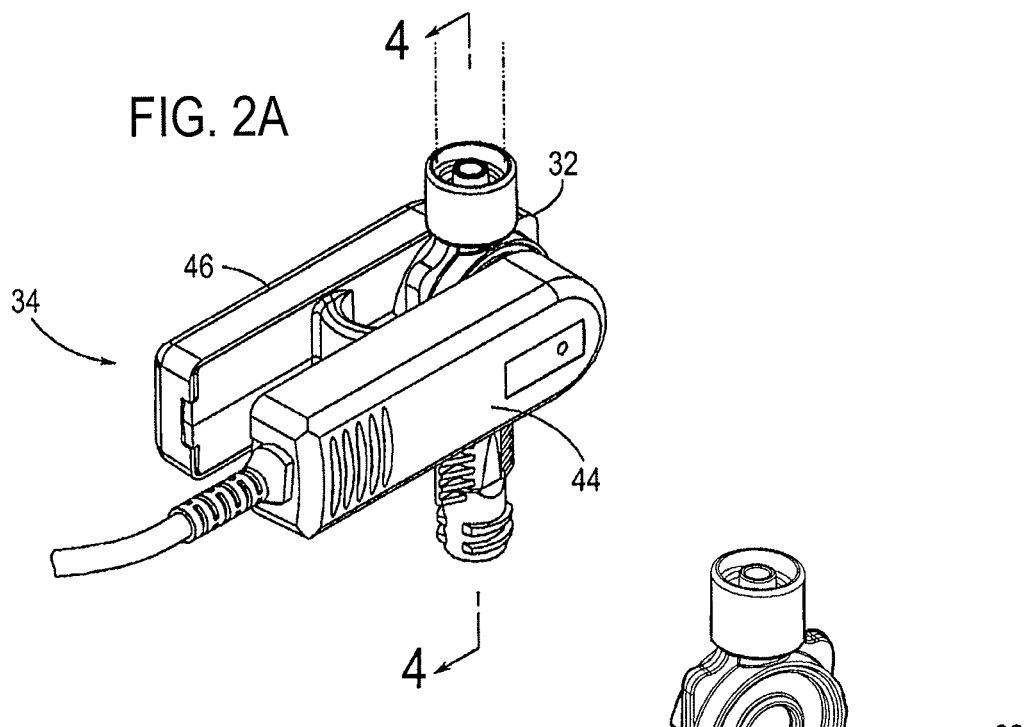
FIG. 2A is a perspective view of the sensor clip assembly and blood chamber of FIG. 1.
Figure 2B:
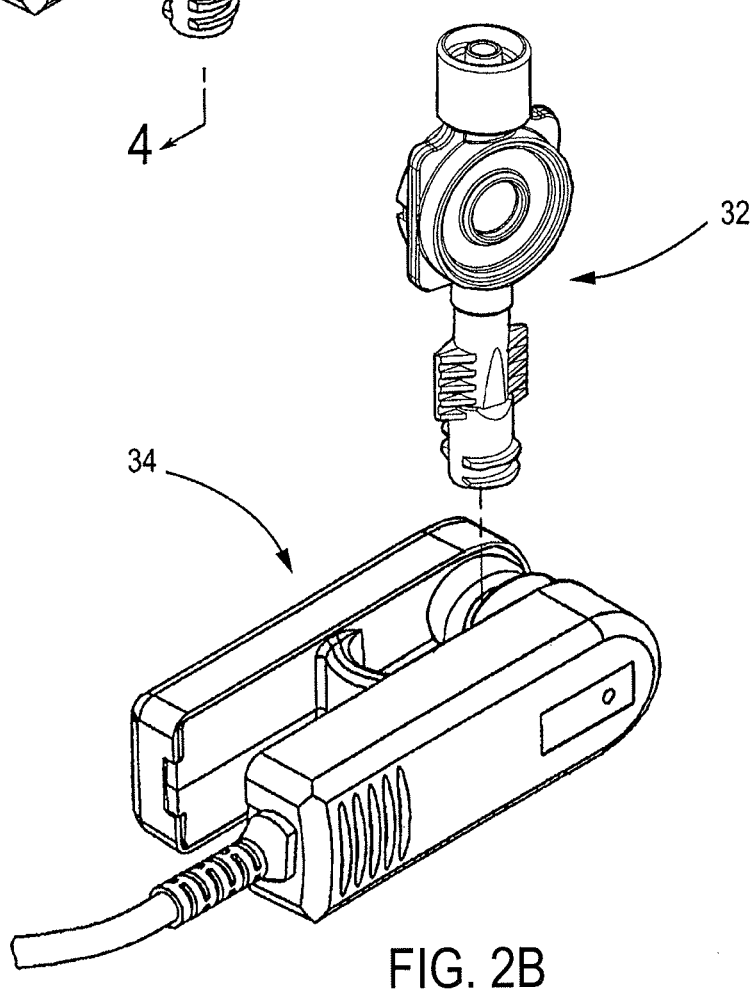
FIG. 2B is the perspective view of FIG. 2A with the a blood chamber removed from the clip assembly in order to better view the blood chamber.
Figure 3B:
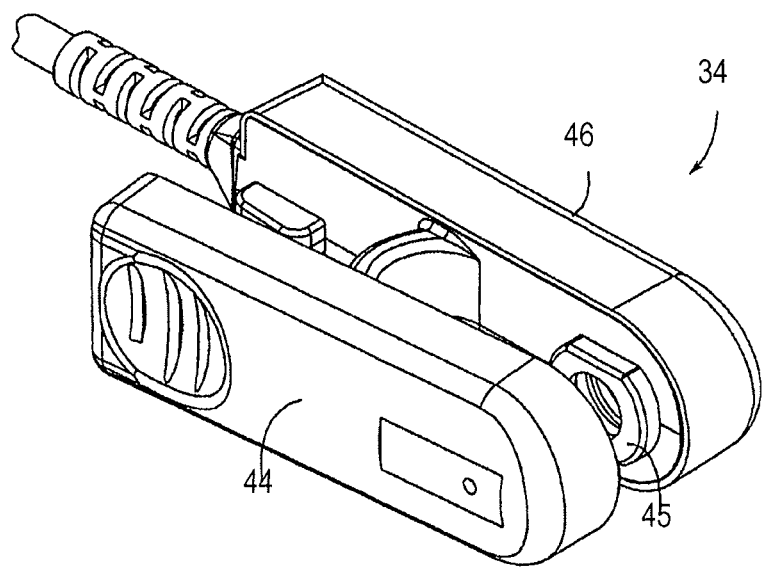
FIG. 3B is an isolated view of the sensor clip assembly shown in FIGS. 1 and 2A.
Figure 4A:
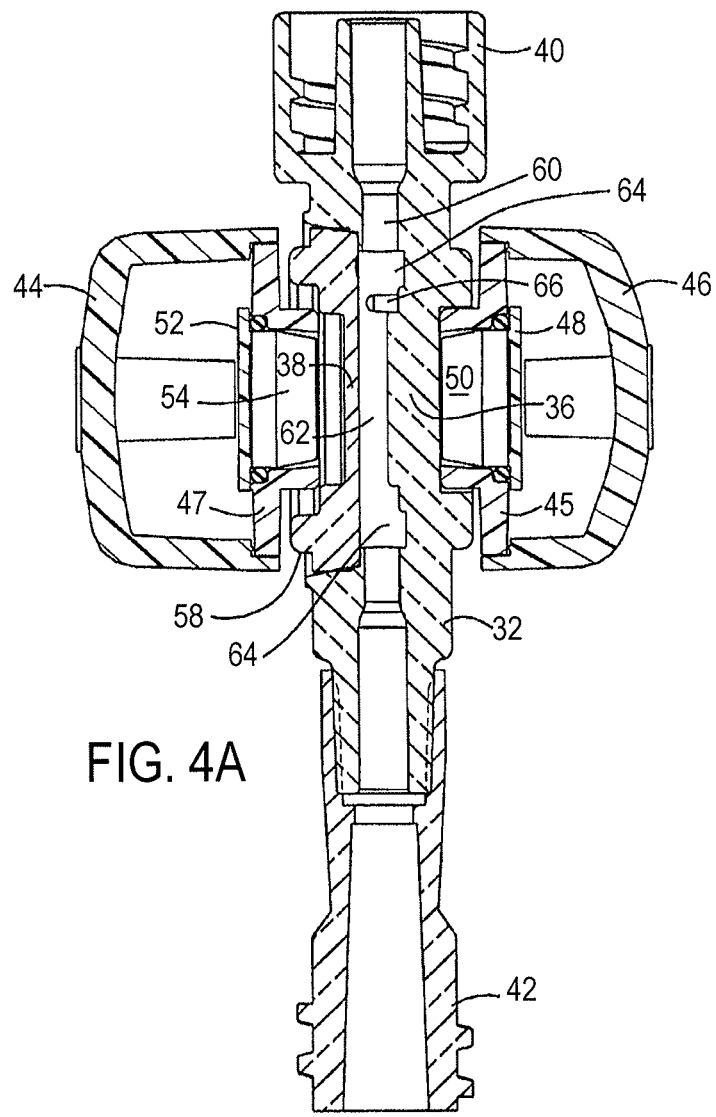
FIG. 4A is a longitudinal, cross-sectional view of the blood chamber and sensor clip assembly taken along line 4-4 in FIG. 2A.

The sensor assembly 34 includes emitter and detector subassemblies 44 and 46, respectively. Referring to FIGS. 3B and 4A, each of the emitter and detector subassemblies 44 and 46 has a head portion 47 and 45, respectively. Referring to the cross sectional view in FIG. 4A, each side of the heads 45, 47 provides an opening into which the molded diffusion lenses 50, 54 are mounted. The sensor assembly 34 is a spring-loaded clip assembly adapted to be removably mounted to the blood chamber 32, as shown in FIG. 2A.

Figure 3A:
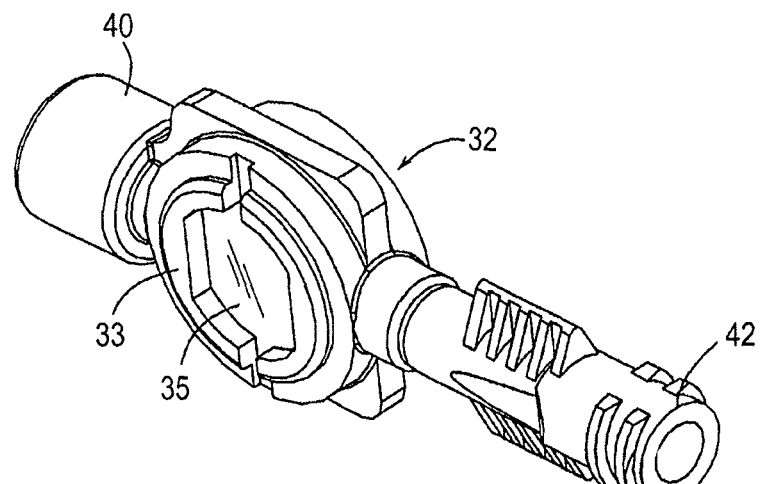
FIG. 3A is an isolated view of the blood chamber shown in FIGS. 1 and 2A.

Each of the heads 47 and 45 has a double-D configuration complementing the double-D configuration of the blood chamber 32 as best seen in FIG. 3A. The interlocking double-D configuration fixes the sensor clip 34 in a predetermined position both laterally and rotationally when it is fastened to the blood chamber 32 as illustrated in FIG. 2A. Fixing the sensor clip 34 in a predetermined position significantly reduces system noise induced by an otherwise freely rotating sensor on the blood chamber. As will be appreciated from the several embodiments illustrated hereinafter, various mechanical arrangements are contemplated for fixing the sensor clip assembly 34 onto the blood chamber so as to correctly position the photoemitters and photodetectors with respect to viewing windows of the blood chamber.

One side of the blood chamber 32 is molded to have a double-D configuration that complements and receives the double-D configuration of head 45 of the sensor assembly 34 in order to fix the assembly in a predetermined position with respect to the blood chamber 32 when the assembly and blood chamber are fastened together. As mentioned, blood chamber 32 is a single-use clear polycarbonate component. Between patient treatments, the blood chamber 32 is replaced along with the extracorporeal tubing 18, 24, and blood filter 22.

Figure 4B:
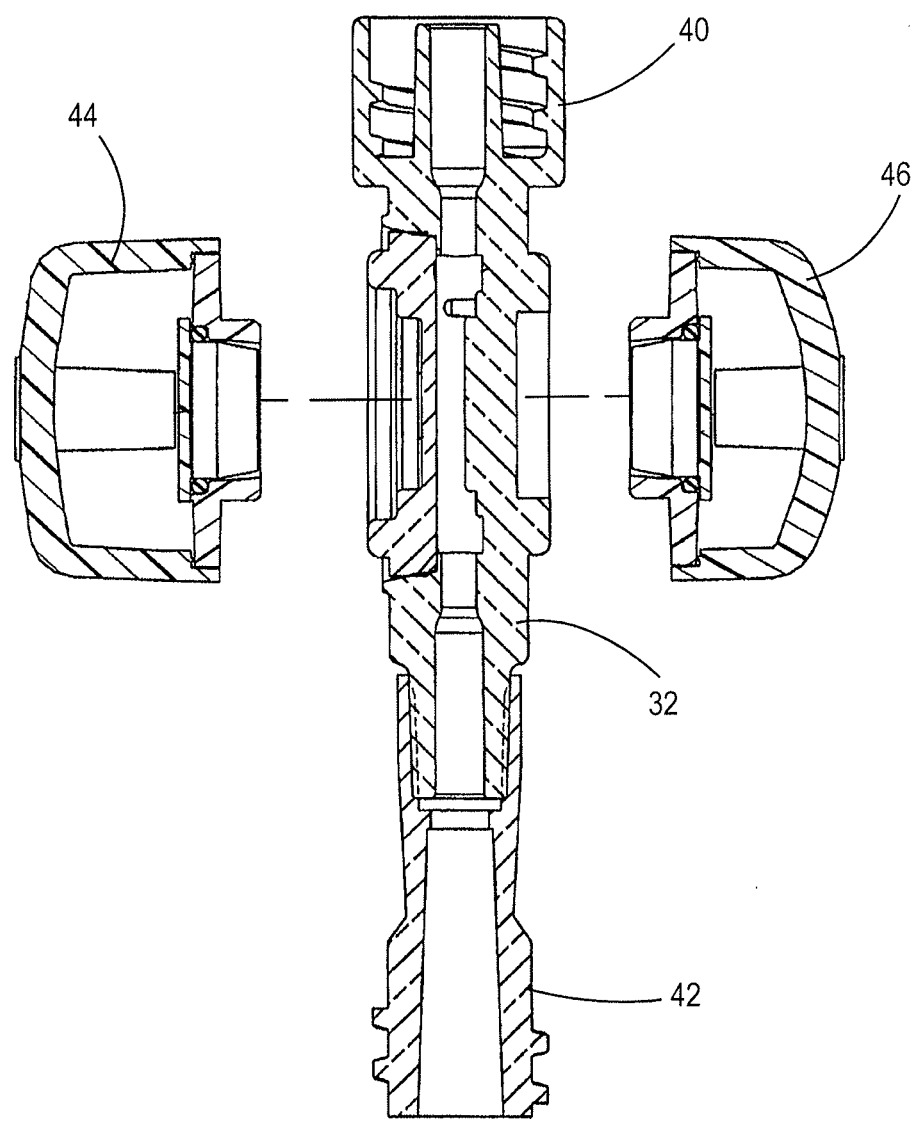
FIG. 4B is the cross-sectional view of the blood chamber and sensor clip assembly in FIG. 4A with the clip assembly exploded away from the blood chamber.

As best shown in FIGS. 4A and 4B, an emitter circuit board 48 containing LEDs emitting light at substantially 660 nm, 810 nm and 1300 nm is mounted within the housing for the sensor subassembly 46. The photoemitters on the LED circuit board 48 emit visible and infrared light through a molded lens 50 mounted in the head 45. They direct visible and infrared light through the viewing window 36 for the blood chamber 32. The controller 35 (FIG. 1), controls the operation of the respective LED emitters and detector(s) in order to multiplex the independent wavelength measurements so that the emitter and respective detector measurements remain correlated.

Another circuit board 52 contains photodetectors, at least one made of silicon to detect light intensity at substantially 810 nm and 660 nm, and at least one made of InGaAs to detect light intensity at 1300 nm. The detector circuit board 52 is mounted within the housing for the detector subassembly 44. A molded lens 54 is mounted in the head 47 of the subassembly 44. The controller 35 includes data acquisition hardware and software which receives signals proportional to the intensities detected by the InGaAs and Si detector diodes.

The viewing window 38 in the blood chamber 32 facilitates transmission of visible and infrared light at the respective wavelengths to the detectors on the circuit board 52 of the detector subassembly 44. Note that the viewing window 38 is molded into a separate insert 58 (referred to as the lens body 58) that is sonically welded to the body of the blood chamber 32. Blood flows from the inlet 40 through the passageway 60 to a central viewing region 62, also referred to herein as an internal blood flow cavity 62. The internal blood flow cavity provides a substantially flat, thin (e.g., less than 0.1 inches) viewing region for the blood flowing through the blood chamber 32. The multiplexed visible or infrared light at the three selected wavelengths, namely about 810 nm, 1300 nm and 660 nm, are transmitted through the blood flowing through the flat viewing region provided by internal blood flow cavity 62, as well as through the viewing windows 36, 38 in the chamber 32. A moat 64 surrounds the flat viewing region 62. The moat 64 is somewhat deeper than the flat viewing region 62. The moat helps distribute non-laminar flow evenly and steadily through the viewing region and provides a region of higher volume blood which under most operating conditions optically isolates the detectors from detecting ambient or ducted light that does not pass through the direct path through the blood in the blood flow chamber. One or more turbulence posts 66 are located immediately upstream of the viewing region 62 to create steady eddy currents in the flow across the viewing region 62.

FIG. 5A is a schematic illustration of a blood chamber 32 with a patient's blood 82 flowing through the chamber 32. As described above, the blood 82 enters the blood chamber through an inlet 40 and then flows into a moat 64 surrounding the flat viewing area 62. The distance across the viewing area 62 is given by the arrow labeled $d_b$, which signifies the thickness of the blood flowing through the flat viewing area 62. After the blood leaves the flat viewing area 62, it flows into the moat 64 located on the other side of the viewing area 62 and out of the chamber through the outlet 42. FIG. 5A shows three LED emitters 84, 86 and 88. LED 84 emits infrared light at substantially 1300 nm, LED 86 emits infrared light at substantially 810 nm, and LED 88 emits red light at substantially 660 nm. As mentioned, each of the LEDs 84, 86, 88 emits light at a fixed average intensity. The LEDs are pulsed on for a time period such that any given LED is on at a time when the other LEDs are not on (i.e., timed-based multiplexing), although other methods of multiplexing are possible. As shown in FIG. 5A, light from each LED emitter 84, 86, and 88 is first transmitted through the clear polycarbonate transmission window 90 in the blood chamber 32, then through the blood flowing through the flat viewing region 62, and finally transmitted through the clear polycarbonate receiving window 92 on the other side of the blood chamber 32. An indium gallium arsenide detector 93 detects the intensity of the 1300 nm light wave that is transmitted through the walls of the blood chamber 32 and the blood flowing through the flat viewing region 92. A silicon detector 95 detects the intensity of the light at 810 nm and at 660 nm transmitted through the walls of the blood chamber 32 and the blood flowing through the flat viewing region 62.

The mathematical ratiometric model for determining the hematocrit (HCT) value can be represented by the following equation:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right] \quad \text{Eq. (1)}$$

where $i_{\lambda 2}$ is the infrared light intensity detected by the photoreceiver at about 810 nm, $i_{\lambda 1}$ is the infrared intensity detected at 1300 nm and $I_{0-\lambda 2}$ and $I_{0-\lambda 1}$ are constants representing the infrared light intensity incident on the blood accounting for losses through the blood chamber. The function $f$ is a mathematical function which has been determined based on experimental data to yield the hematocrit value. Preferably, the function $f$ in the above Equation (1) is a relatively simply polynomial, e.g., a second order polynomial. The above Equation (1) holds true only if the distance traveled by the infrared light radiation from the LED emitters to the photodetectors at both wavelengths are constant distances and preferably the same distance.

The preferred wavelengths to measure oxygen saturation level are about 810 nm and about 660 nm. The mathematical ratiometric model for determining oxygen saturation level (SAT) can be represented by the following equation:

$$SAT = g\left[\frac{\ln\left(\frac{i_{\lambda 3}}{I_{0-\lambda 3}}\right)}{\ln\left(\frac{i_{\lambda 1}}{I_{0-\lambda 1}}\right)}\right] \quad \text{Eq. (2)}$$

where $i_{\lambda 3}$ is the light intensity of the photoreceiver at 660 nm, $i_{\lambda 1}$ is the detected intensity at 810 nm, and $I_{0-\lambda 3}$ and $I_{0-\lambda 1}$ are constants representing the intensity incident on the blood accounting for losses through the blood chamber. The function g is a mathematical function determined based on experimental data to yield the oxygen saturation level, again preferably a second order polynomial. Also, like Equation (1) for the hematocrit calculation, Equation (2) for the oxygen saturation level calculation holds true only if the distance traveled by the visible and infrared light from the respective LED emitter to the respective detector at both the 660 nm and 810 nm wavelengths are constant distances and preferably the same distance.

The intensity of the light at each of the various wavelengths is reduced by attenuation and scattering from the fixed intensity of the light emitted from each of the LEDs 84, 86, 88. Beers Law, for each wavelength of light, describes attenuation and scattering as follows:

$$i_n = I_{o-n} e^{-\epsilon_p X_p d_{pt}} e^{-\epsilon_b X_b d_b} e^{-\epsilon_p X_p d_{pr}} \qquad (3)$$

where $i_n$=received light intensity at wavelength n after attenuation and scattering; $I_{o-n}$ is the transmitted light intensity at wavelength n incident to the measured medium; e is the natural log exponential term; $\epsilon$ is the extinction coefficient for the measured medium (p=polycarbonate, b=blood); X is the molar concentration of the measured medium (p=polycarbonate, b=blood); and d is the distance through the measured medium (pt=transmitting polycarbonate, b=blood, pr=receiving polycarbonate).

Since the properties of the polycarbonate blood chamber do not change, the first and third exponential terms in the above Equation (3) are normally assumed to be constants for each wavelength. Mathematically, these constant terms are multiplicative with the initial constant term $I_{o-n}$ which represents the fixed intensity of the radiation transmitted from the respective LED emitter 84, 86, and 88. For simplification purposes, Equation (3) if often rewritten in the following form using bulk extinction coefficients and a modified initial constant $I'_{o-n}$ as follows:

$$i_n = I'_{o-n} * e^{-\alpha_b d_b} \qquad \text{Eq. (4)}$$

where $i_n$ is the received light intensity at wavelength n after attenuation and scattering as though the detector were at the blood boundary; $\alpha$ is the bulk extinction coefficient for blood; $\alpha_b = \epsilon_b X_b$; and $I'_{o-n}$ is the equivalent transmitted radiation intensity at wavelength n boundary accounting for losses through the blood chamber walls.

Using the approach defined in Equation (4) above, the 810 nm wavelength, which is isobestic for red blood cells, and the 1300 nm wavelength, which is isobestic for water, can be used to determine the patient's hematocrit. The ratio of the normalized amplitudes of the measured intensity at these two wavelengths produces the ratio of the composite extinction values α for the red blood cells and the water constituents in the blood chamber, respectively. Therefore, the following mathematical function defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \qquad \text{Eq. (5)}$$

where $i_{810}$ is the detected infrared intensity of the photoreceiver 95 (FIG. 5A) at 810 nm, $i_{1300}$ is the detected infrared intensity of the photodetector 93 (FIG. 5A) at 1300 nm, and $I_{0-810}$ and $I_{0-1300}$ are constants representing the infrared light intensity incident on the blood accounting for losses through the blood chamber at 810 nm and 1300 nm, respectively. The above equation holds true assuming that the flow of blood through the blood chamber 32 is in steady state, i.e., the viewing area 62 is completely full of the blood under test. The preferred function $f$ is a second order polynomial having the following form:

$$HCT = f\left[\frac{\ln\left(\frac{i_{810}}{I_{0-810}}\right)}{\ln\left(\frac{i_{1300}}{I_{0-1300}}\right)}\right] = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \qquad \text{Eq. (6)}$$

A second order polynomial is normally adequate as long as the infrared radiation incident at the first and second wavelengths is substantially isobestic.

The oxygen saturation level, or the oxygenated hemoglobin level, is determined using a ratiometric equation for the intensity of red light at 660 nm detected by detector 95 (see FIG. 5A) and the intensity of infrared light at 810 nm detected by detector 95 (see FIG. 5A). The form of the ratiometric model for determining oxygen saturation level is as follows:

$$SAT = g\left[\frac{\ln\left(\frac{i_{660}}{I_{0-660}}\right)}{\ln\left(\frac{i_{810}}{I_{0-810}}\right)}\right] \qquad \text{Eq. (7)}$$

where $i_{660}$ is the detected intensity of the photoreceiver at 660 nm, $i_{810}$ is the detected intensity of the photodetector at 810 nm and $I_{0-660}$ and $I_{0-810}$ are constants representing the light intensity incident on the blood accounting for losses through the blood chamber. The function g is a mathematical function based on experimental data to yield the oxygen saturation level, again preferably a second order polynomial:

$$SAT = g\left[\frac{\ln\left(\frac{i_{660}}{I_{0-660}}\right)}{\ln\left(\frac{i_{810}}{I_{0-810}}\right)}\right] = A\left[\frac{\ln\left(\frac{i_{660}}{I_{0-660}}\right)}{\ln\left(\frac{i_{810}}{I_{0-810}}\right)}\right]^2 + B\left[\frac{\ln\left(\frac{i_{660}}{I_{0-660}}\right)}{\ln\left(\frac{i_{810}}{I_{0-810}}\right)}\right] + C. \qquad \text{Eq. (8)}$$

FIG. 5B is a schematic drawing similar to FIG. 5A further illustrating the effect of ambient ducted light that does not pass through a direct path through the blood in the blood flow chamber. In this regard, ray 96 is illustrative of ambient or ducted light. If ambient or ducted light is sensed by the detectors 93, 95, measurement inaccuracies can occur if not appropriately accounted for by signal processing. It has been found desirable to physically eliminate the effect of ambient light that might otherwise be detected by the photodetectors 93, 95. As mentioned, this is done by providing shrouds on the sensor clip assembly and providing a single-use blood chamber with a mating configuration. It is also desirable to construct the chamber body of an opaque material to further attenuate ambient light.

A signal ray 96 of ducted light radiation is shown in FIG. 5B, and in particular, a single ray of red light having a wavelength of about 660 nm that is sensed by the photodetector 95. Light piping occurs when the incident angle of the light from the LED (e.g., 660 nm light wave from the LED 88) at the boundary of the chamber 32 and the blood 82 is smaller than the critical angle defined by Snell's Law. In this circumstance, the light reflects into the blood chamber material 32 rather than passing through the blood 82 directly to the photodetector 95. Due to the geometry of the blood chamber 32 and the ability of its clear polycarbonate material to transmit light via reflection/refraction, ducted light can take many unique paths prior to being refracted towards the detector 95. In actuality, the resulting signal at the photodetector 95 is the summation of all direct and all piped rays that arrive at that location. Because the wavelength of the light is comparatively small, virtually any change in the manufacturing tolerance from blood chamber to blood chamber will negate any ability to fully and predictably characterize a transfer function for the piped or ducted light. Ducting is a function (but not limited to) the material of the blood chamber 32, the blood chamber dimensions, the number of reflections/refractions from the LED emitter to the photodetector, the wavelength of the light or infrared radiation, and the total path of distance traveled. For simplicity and analysis, the intensity of piped light at the detector ($i_p$) is a function of several variables:

$$i_p = \rho(v_1, v_2, v_3 \ldots v_n) I o \qquad \text{Eq. (9)}$$

where:
  $I_o$=the impressed intensity from the LED photoemitter at the wavelength of interest;
  $i_p$=the received intensity from the direct piping path at the photodetector;
  p=the piping function of several variables: $v_1, v_2, v_3, \ldots v_n$ The total intensity received at the photodetector 95 will be the resultant sum of the individual light signals arriving at the photodetector 95. Because light exhibits both particle and wave characteristics, it is reasonable to conclude that this summation will be in vector form comprised of the vector sums of the amplitude at the respective phases of each respective light component. In general:

$$i = i_s + i_p \qquad \text{Eq. (10)}$$

where:
  i=the total intensity signal summed and integrated into a current at the photodetector
  $i_s$=the component of light arriving from the LED 88 along the signal path $d_b$
  $i_p$=the component of light arriving from the LED 88 through light piping paths.

With ducting present, Equation (8) must be modified by $i_p$ added to each ratiometric term $i_s$. Since $i_p$ and the ratiometric term $i_s$ do not change proportionally, the polynomial g has no solution and cannot be determined if the value of $i_p$ is significant compared to the ratiometric term $i_s$.

Considering that the total intensity signal i includes both the component $i_s$ for the direct signal path $d_b$ and the components of ducted light $i_p$, it becomes difficult if not impossible to determine an adequately reliable function g for the above Equation (7) over the full dynamic range necessary to measure oxygen saturation levels when the patient's hematocrit is low so that the light piping signals 96 are not attenuated by blood in moat 64 of the blood chamber 32. Efforts to mathematically account for light piping errors have to date been difficult to achieve. It has been found that the preferred method is to eliminate the intensity of piped light detected by the photodetector 95. This is done by adding materials or tinting to the blood chamber body that attenuate the light at the appropriate wavelengths as it travels through the blood chamber body, thereby eliminating light piping terms from the necessary mathematics for the ratiometric model.

Figure 6:
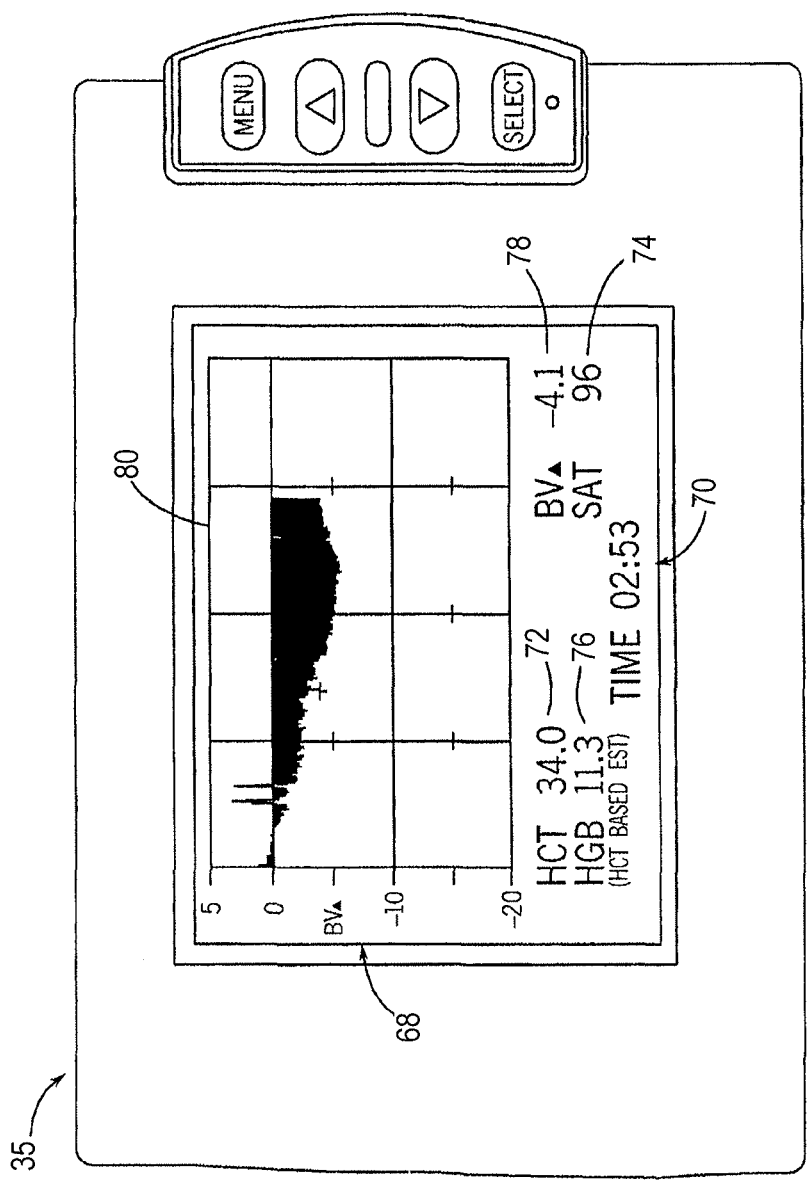
FIG. 6 is a front elevational view of the controller for the optical blood monitor illustrating data including real-time hematocrit (HCT), change in blood volume (BVΔ), hemoglobin (HBG), and oxygen saturation (SAT) levels, as well as the amount of time into the hemodialysis treatment session and a graphical representation of the change in blood volume during the course of the hemodialysis treatment session.

FIG. 6 is a front elevational view of an exemplary controller 35 for the optical blood monitor 14. The controller 35 includes a display 68 that provides real-time blood monitoring data for the patient undergoing hemodialysis. The display 68 in FIG. 6 illustrates the amount of time 70 that the patient 10 has been undergoing hemodialysis for the current treatment session. The time 70 displayed on the screen 68 in FIG. 6 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ) during the treatment session. The graph 80 on the display 68 illustrates the change in the patient's blood volume over the course of the 2 hour and 53 minute treatment session. This data is displayed, as shown in FIG. 1, in a location that is located within the vicinity of the patient 10.

First Embodiment

Figure 10:
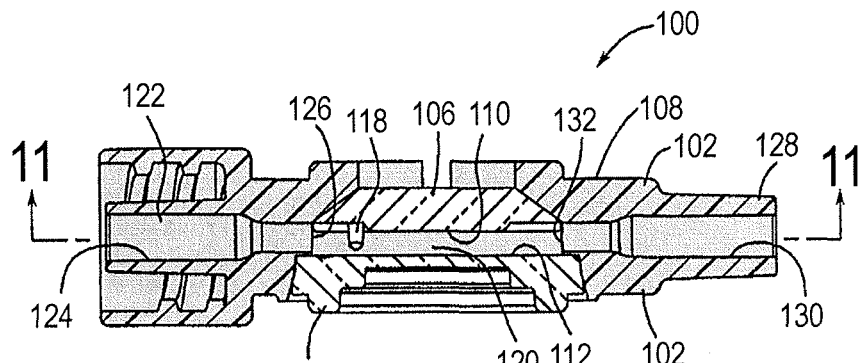
FIG. 10 is a longitudinal sectional view taken along line 10-10 in FIG. 7.
Figure 11:
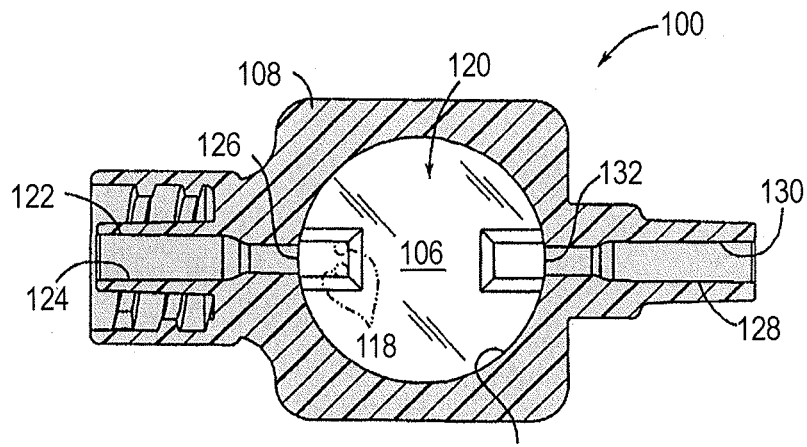
FIG. 11 is a sectional view taken along line 11-11 in FIG. 10.

FIGS. 7 through 11 illustrate a blood chamber 100 in accordance with the first illustrated embodiment. Structurally, the blood chamber 100 is similar in many respects to the conventional blood chamber 32 shown in FIGS. 3A and 4A; however, the blood chamber 100 has a chamber body 102 that includes a blue-tinted portion 108 in order to attenuate light ducting at the 660 nm wavelength. Referring in particular to FIG. 10, the window 106 on the chamber body 102 is preferably made of clear, medical grade polycarbonate material which is molded with a polished finish in order to facilitate reliable light transmission, e.g., Bayer Makrolon FCR2458-55115 (no regrind allow), which is blood contact approved, USP XX11, Class V1. It is expected that the material be certified as to grade number, lot number, and date of manufacture.

No mold release should be used, and any lubrications should be food grade and not silicon-based. The molded parts should be produced with no loose foreign material greater than 0.1 mm² and no embedded foreign material greater than 0.2 mm². The mold finish is preferably SPIA3 (scale) except along the surfaces for the viewing windows in which the finish is preferably at least SPIA1. Moreover, the viewing windows should contain no splay, bubbles or marks when looking through the display window viewed from 12 inches with the normal eye. Parts should be cleaned and free of dirt, oils and other foreign matters before use. The clear window 106 is preferably molded prior to overmolding the remaining blue-tinted portion of the chamber body 102. More specifically, the clear window 106 is placed in the mold, while the blue-tinted portion 108 of the chamber body is overmolded. The material of the blue-tinted portion 108 should be compatible with the material of the clear window 106, and preferably is the same material (medical grade polycarbonate) except for the tinting. Compatibility of the materials is important because it is unacceptable for leaking to occur at the seam between the clear window 106 and the remaining blue-tinted portion 108.

The blue-tinted portion 108 is preferably tinted in a dark blue which is opaque and not transparent to red light in general, and in particular red light having a wavelength of about 660 nm. A suitable blue-tint for the polycarbonate material for this purpose is Pantone PMS 2935.

It should be noted that the blood chamber 100 in FIGS. 7-11 does not include a moat surrounding the viewing area within the blood flow cavity 120. As mentioned, it may be desirable to remove the moat from the blood chamber if the system is able to eliminate the effects of ambient light, for example through the use of appropriate signal processing.

The window body 104 is preferably made entirely of clear, medical grade polycarbonate, and is sonically welded into place on the chamber body 102. The overmolded window 106 in the chamber body 102 includes a substantially flat internal wall 110 which forms part of the internal blood flow cavity 120. The window body 104 includes a substantially flat internal wall 112.

The chamber body includes a substantially flat internal wall 110 which forms part of the internal blood flow cavity 120. When the window 104 is attached to the chamber body 102, the flat internal wall 112 on the window body is substantially parallel to the flat internal wall 110 on the chamber body 102. The flat internal wall 112 on the window 104 is separated from the flat internal wall 110 on the chamber body 102 by a predetermined fixed distance. The clear portions 106 on the overmolded chamber body 102 and the window 104 commensurate with at least a portion of the flat internal walls 110, 112 serve as viewing windows for blood flowing through the internal blood flow cavity 120. The blood flow cavity 120 is defined by the flat internal walls 110, 112 as well as a peripheral wall 114 (FIG. 8) on the chamber body 102 that extends between the periphery of the flat internal walls 110, 112 when the window 104 is welded into place. The chamber body 102 includes a first port 122 and a channel 124 which are in fluid communication through a first opening 126 in the peripheral wall 114 with the internal blood flow cavity 120. The chamber body 102 also includes a second port 128 and channel 130 which are in fluid communication through a second opening 132 in the peripheral wall 114 with the internal blood flow cavity 120. In the embodiment shown on FIGS. 7 through 11, the second port 128 and channel 130 are in axial alignment with the first port 122 and channel 124 along an axis that spans across the middle of the internal blood flow cavity 120. As mentioned, the internal flow cavity 120 in the embodiment shown in FIGS. 7-11 does not include a moat around the periphery of the viewing area.

The chamber body 102 also includes a pair of turbulence posts 118 which ensure robust, non-laminar flow through the viewing area in the internal blood flow cavity 120. By disrupting laminar flow through the chamber, the posts 118 ensure the cavity of the chamber fills with blood. The flow resistance provided by the posts 118 create eddy currents in the cavity that also help mix the blood to make it more homogeneous when measured. In order to provide the function of filling the cavity of the blood chamber and mixing the blood, the posts 118 must be on the inlet side of the chamber 100. In the illustrated embodiment, the first port 122 is the inlet port. However, the second port 128 could alternatively be the inlet port. In that case, referring to FIG. 10, the posts 118 would be located on the right hand side of the cavity so that blood is intercepted by the posts upon entry into the cavity of the blood chamber. The posts 118 need to be on the upstream side of the cavity to be effective.

Figure 7:
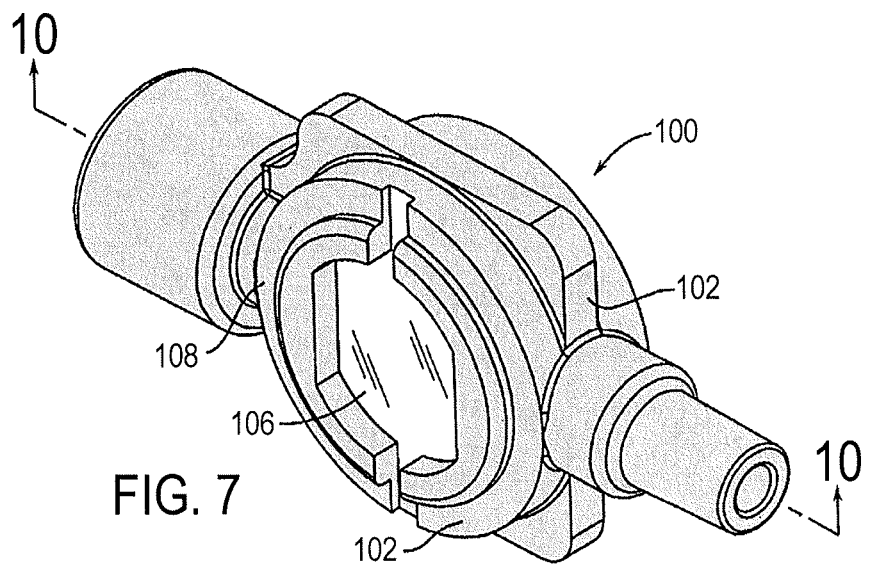
FIG. 7 is a perspective view of a blood chamber constructed in accordance with the first embodiment.
Figure 8:
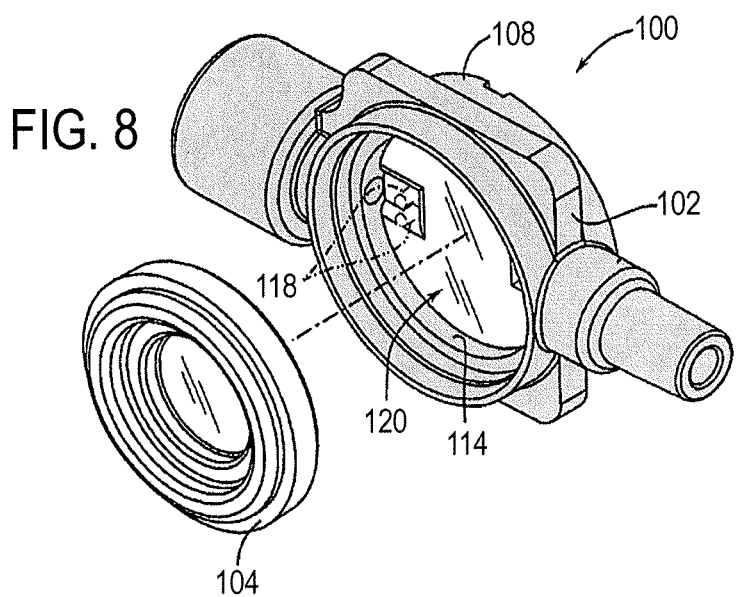
FIG. 8 is a view similar to FIG. 7 showing a window body exploded away from a chamber body.
Figure 9:
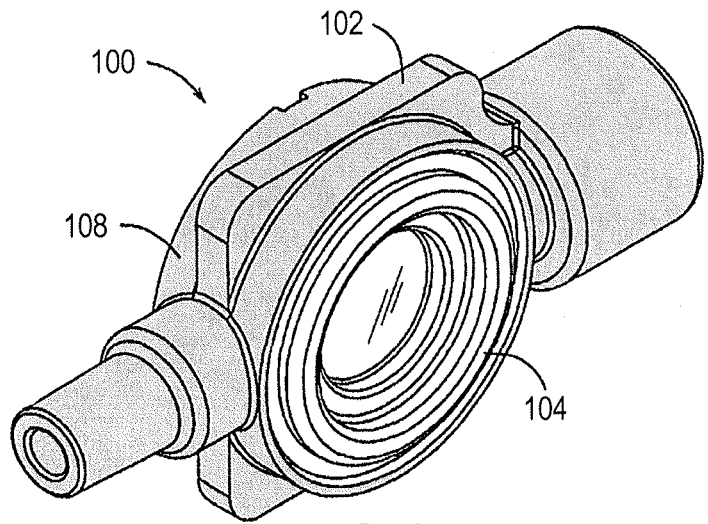
FIG. 9 is a perspective view of the back side of the blood chamber shown in FIGS. 7 and 8.

The blood chamber 100 fastens to the clip assembly in substantially the same manner as illustrated and described in connection with the introductory embodiment illustrated in FIGS. 1-6. As best illustrated in FIG. 7, the blood chamber 100 includes an annular rim whose inner circumference defines a double-D configuration much like that of the blood chamber 32 in FIG. 3A. The interlocking double-D configuration fixes the sensor clip 34 in a predetermined position both laterally and rotationally when it is fastened to the blood chamber 32 as illustrated in FIG. 2A.

Second Embodiment

Figure 12:
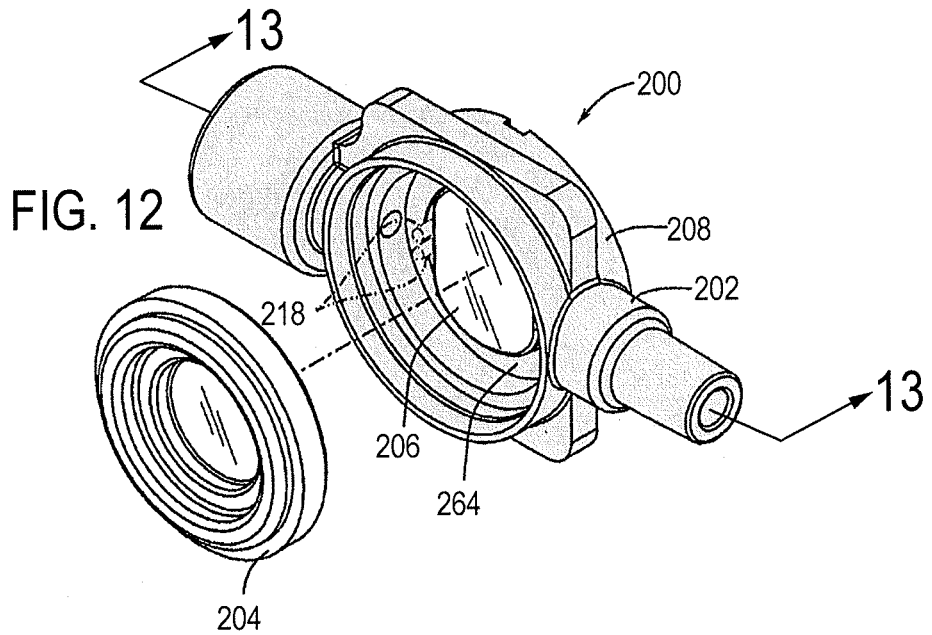
FIG. 12 is a view similar to FIG. 8 illustrating a second embodiment.
Figure 13:
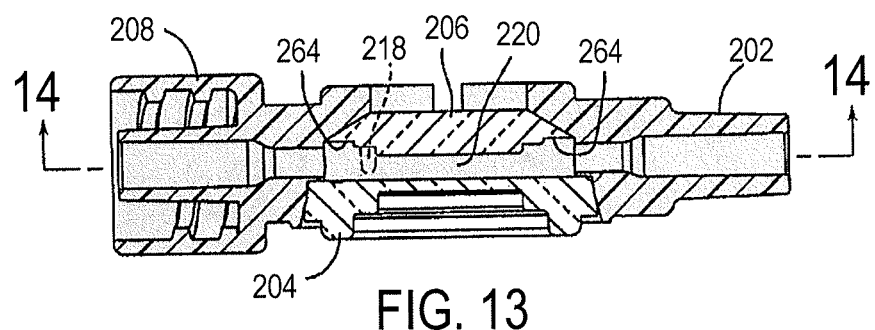
FIG. 13 is a longitudinal sectional view of the second embodiment.
Figure 14:
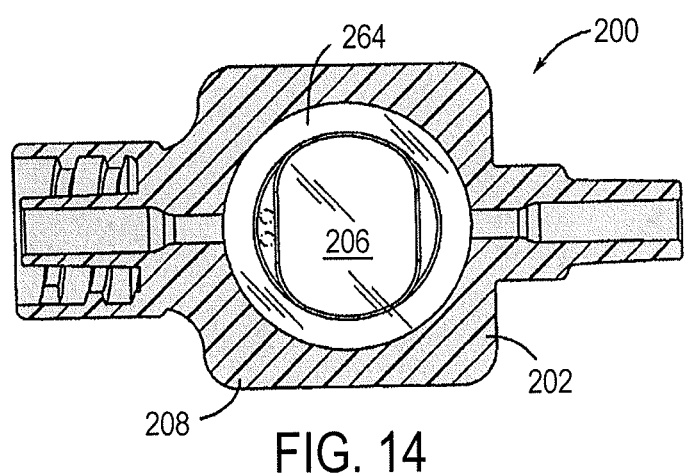
FIG. 14 is a sectional view taken along line 14-14 in FIG. 13.

FIGS. 12 through 14 illustrate a blood chamber 200 constructed in accordance with a second illustrated embodiment. Blood chamber 200 includes a moat 264 surrounding the internal blood flow cavity 220 as in the conventional blood flow chamber 32 illustrated in FIGS. 3A and 4A. In fact, the structure and dimensions of the blood chamber 200 shown in FIGS. 12 through 14 are substantially the same as those shown in the blood chamber 32, with the primary difference being that portion 208 of the blood chamber body 202 is made of a blue-tinted material, such as the dark blue tinted polycarbonate of the first embodiment, in order to attenuate ducted red light particularly at 660 nm if the LED emitter 88 emits red light at 660 nm. Because of the presence of the moat 264, ducting of the infrared radiation through the chamber body 202 (or ambient light) is even less likely to cause errors in the mathematics pertaining to the ratiometric models for determining the real-time oxygen saturation and hematocrit levels.

As with the blood chamber 100 shown in FIGS. 7 through 11, the viewing window 206 on the chamber body 202 is preferably made of clear, polished polycarbonate material, and the remaining portion 208 of the chamber body 202 is overmolded to the window 206. As mentioned previously, the opaque (blue-tinted) portion 208 of the chamber body 202 is preferably made of the same material as the clear lens portion 206, but tinted blue in order to block the transmission of red light occurring at the relevant wavelengths, e.g., about 660 nm. As in the previous embodiments, the lens body 204 is made of clear material, e.g., clear polycarbonate, which is sonically welded to the chamber body 202. Also as in the previous embodiment, the blood chamber 200 includes a pair of turbulence posts 218 that ensure robust, non-laminar flow through the viewing area in the internal blood flow cavity 220. The posts are positioned on the upstream side of the cavity as explained in connection with the similar posts in the first embodiment.

The blood chamber 200 fastens to the sensor clip assembly 34 of FIG. 3B in substantially the same manner as illustrated and described above for the blood chambers 32 and 100. Specifically, the blood chamber 200 includes an annular rim whose inner circumference defines a double-D configuration much like that of the blood chambers 32 and 100 in FIGS. 3B and 7, respectively. The interlocking double-D configuration fixes the sensor clip 34 in a predetermined position both laterally and rotationally when it is fastened to the blood chamber 200.

Third Embodiment

Figure 15:
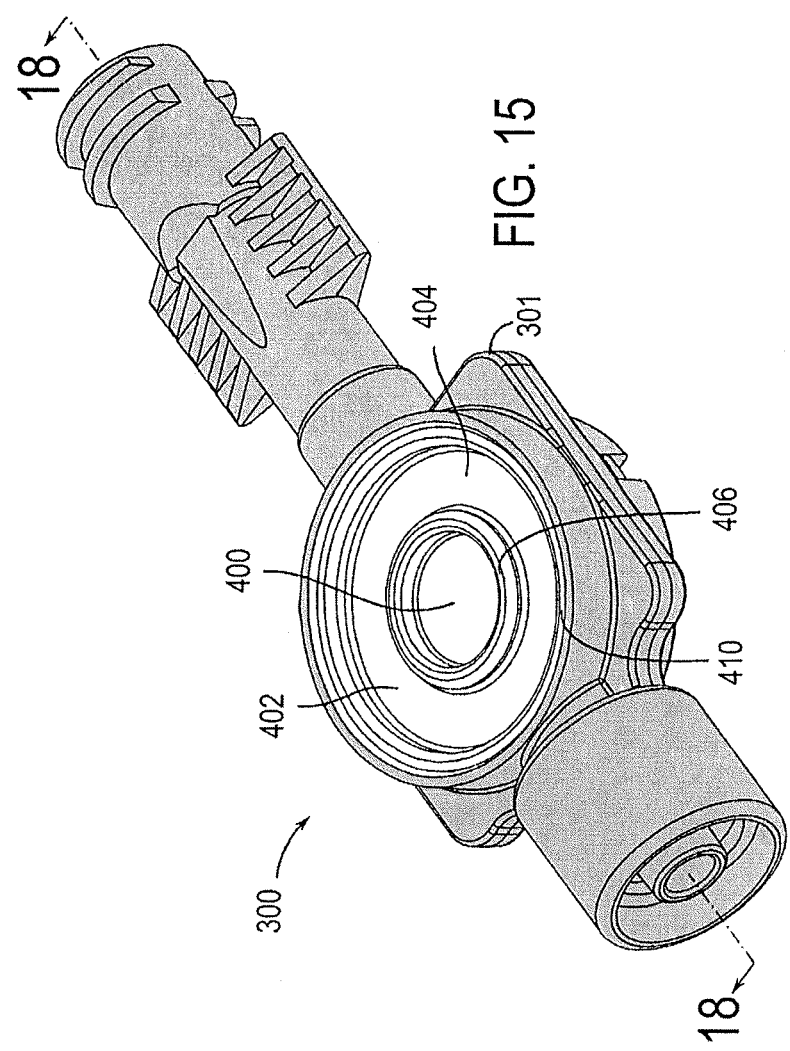
FIG. 15 is a perspective view of one side of a blood chamber constructed in accordance with a third embodiment.

FIGS. 15 through 18 illustrate a blood chamber 300 constructed in accordance with a third illustrated embodiment. This embodiment includes a blue-tinted portion in keeping with the first and second illustrated embodiments and is configured to mate with a sensor clip assembly that includes a shroud for blocking unwanted light from the window of the blood chamber. The blood chamber 300 includes first and second exterior sides as illustrated in FIGS. 15 and 16. Each side has a viewing window and a separate, distinct shroud mating surface located circumferentially around the viewing window. Preferably, on one exterior surface of the blood chamber (FIG. 16), the viewing window is raised above the circumferential shroud mating surface such that a sunken annular well is formed around the raised viewing window. The shape of the floor of the sunken annular well complements the shape of the shroud mating surface on that side of the blood chamber. Preferably, when mounted on the blood chamber the shroud on the clip assembly substantially fills the area of the floor of the sunken annular well, thereby maximizing the amount of unwanted light blocked by the shroud. An upstanding wall on the other exterior surface of the blood chamber (FIG. 15) surrounds the second viewing window and separates it from the shroud mating surface on that side of the blood chamber. In this way, an annular well is formed around the second viewing window, although this annular well is at substantially the same depth as the viewing window on that side of the blood chamber. Again, the shape of the floor of the annular well complements the shape of the shroud mating surface on the exterior side of the blood chamber, and has dimensions substantially the same as the dimensions of the floor of the sunken annular well on the other side of the blood chamber so that the shroud fills the surface area of the floor of the well.

FIG. 16 illustrates a first exterior side of the blood chamber 300. The blood chamber 300 is constructed from a molded chamber body 301 which includes an inlet and an outlet as well as a first viewing window 303. The chamber body 301 may be molded entirely of clear, medical grade polycarbonate material or other suitable material. Alternatively, it may be desirable to use a window insert 302 made of entirely clear, medical grade polycarbonate, and overmold the remaining parts of the chamber body 301 with an opaque material such as the blue-tinted medical grade polycarbonate of the previous embodiments. In either case, the preferred chamber body 301 includes a circular viewing window 303 and a separate, distinct shroud mating surface 304 located circumferentially around the viewing window 303. The shroud mating surface 304 is sunken with respect to the surface of the viewing window 303, and is adapted to receive a shroud on a sensor clip assembly as will be discussed in more detail below. FIG. 16 also illustrates two anti-rotation tabs 307, 308 formed on the exterior surface of the blood chamber 300. The anti-rotation tabs 307, 308 are raised above the surface of the window 303.

FIG. 15 illustrates the other exterior side of the blood chamber 300. This side of the blood chamber 300 includes a second circular viewing window 400. The region between the second viewing window 400 in FIG. 15 and the first viewing window 303 in FIG. 16 consists of material such as clear, medical grade polycarbonate and the blood flowing through the internal blood flow cavity within the blood chamber 300. The windows 303, 400 thus provide an optically neutral view for the sensor clip assembly to monitor the blood flowing through the blood chamber 300. Referring still to FIG. 15, an upstanding annular wall 406 surrounds the second viewing window 400. An annular well 404 is formed between the upstanding, annular wall 406 and a peripheral wall 410 on the blood chamber 300. The floor of this annular well 404 is another shroud mating surface which again is separate and distinct from the viewing window 400. In accordance with the presently preferred embodiment, a window body 402 containing the viewing window 400, the upstanding wall 406, and the surrounding annular well 404, is molded of a clear polycarbonate material and is attached via sonic welding or other means to the chamber body 301 during the manufacturing process.

Figure 18:
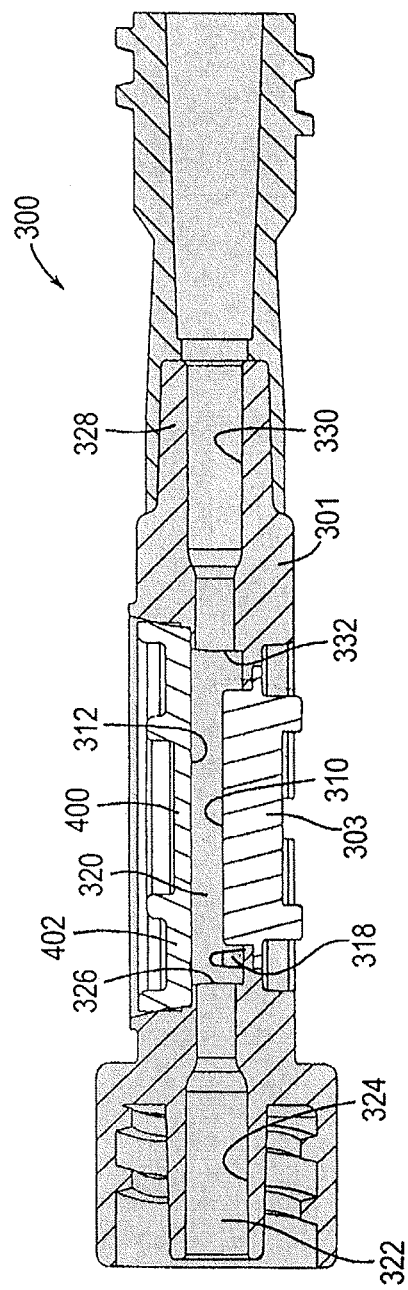
FIG. 18 is a longitudinal, cross-sectional view taken along line 18-18 in FIG. 15.

FIG. 18 shows the cross section of the blood chamber 300. The chamber body 301 includes a substantially flat internal wall 310 that forms part of the internal blood flow cavity 320. The window body 402 attached to the chamber body 301 also includes a substantially flat internal wall 312 that is substantially parallel to the substantially flat internal wall 310 on the chamber body 301. The flat internal wall 312 on the window body 402 is separated from the flat internal wall 310 on the chamber body 301 by a predetermined fixed distance. The first viewing window 303 on the chamber body 301 and the second viewing window 400 on the window body 402 serve as viewing windows 336 and 338 (FIG. 21) for blood flowing through the internal blood flow cavity 320. The chamber body 301 (FIG. 18) includes a first port 322 and a channel 324 (inlet) that are in fluid communication through a first opening 326 in the internal blood flow cavity 320. The chamber body 301 also includes a second port 328 and channel 330 (outlet) that are in fluid communication through a second opening 332 to the internal blood flow cavity 320.

As best seen in FIG. 18, a pair of turbulence posts 318 is positioned at the entrance of the cavity 320. As with the posts of the previous embodiments, the posts 318 provide resistance to suppress any tendency of the blood flow to be a laminar flow, which may result in the blood not filling the cavity 320. The posts also create an eddy current of the blood in the cavity 320, which tends to mix the blood to a more homogenous consistency that provides for better measurements. Because each of the first and second ports 322 and 328 can serve as either an outlet or an inlet, the posts 318 can be on either end of the cavity 320 as explained above in connection with the first and second embodiments. The posts must be positioned at the flow's entrance into the cavity 320 to ensure the posts properly provide the resistance to break up a laminar flow and to create eddy currents to mix the blood before it is measured.

Figure 19:
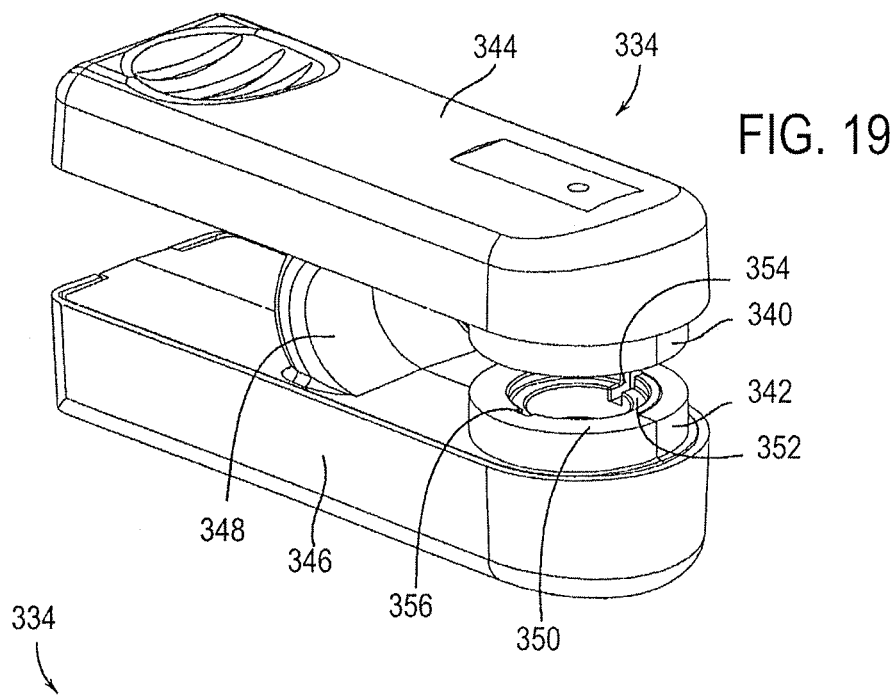
FIG. 19 is a perspective view of an alternative embodiment of the sensor clip assembly for mating to the third embodiment of the blood chamber.
Figure 20A:
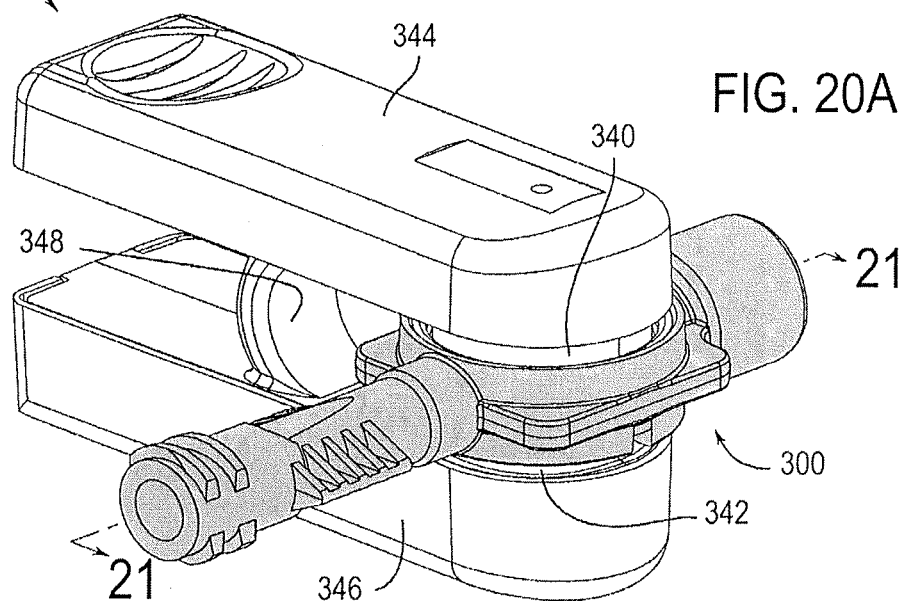
FIG. 20A is the perspective view of the sensor clip assembly of FIG. 19 fastened to the blood chamber of FIGS. 15-18.
Figure 20B:
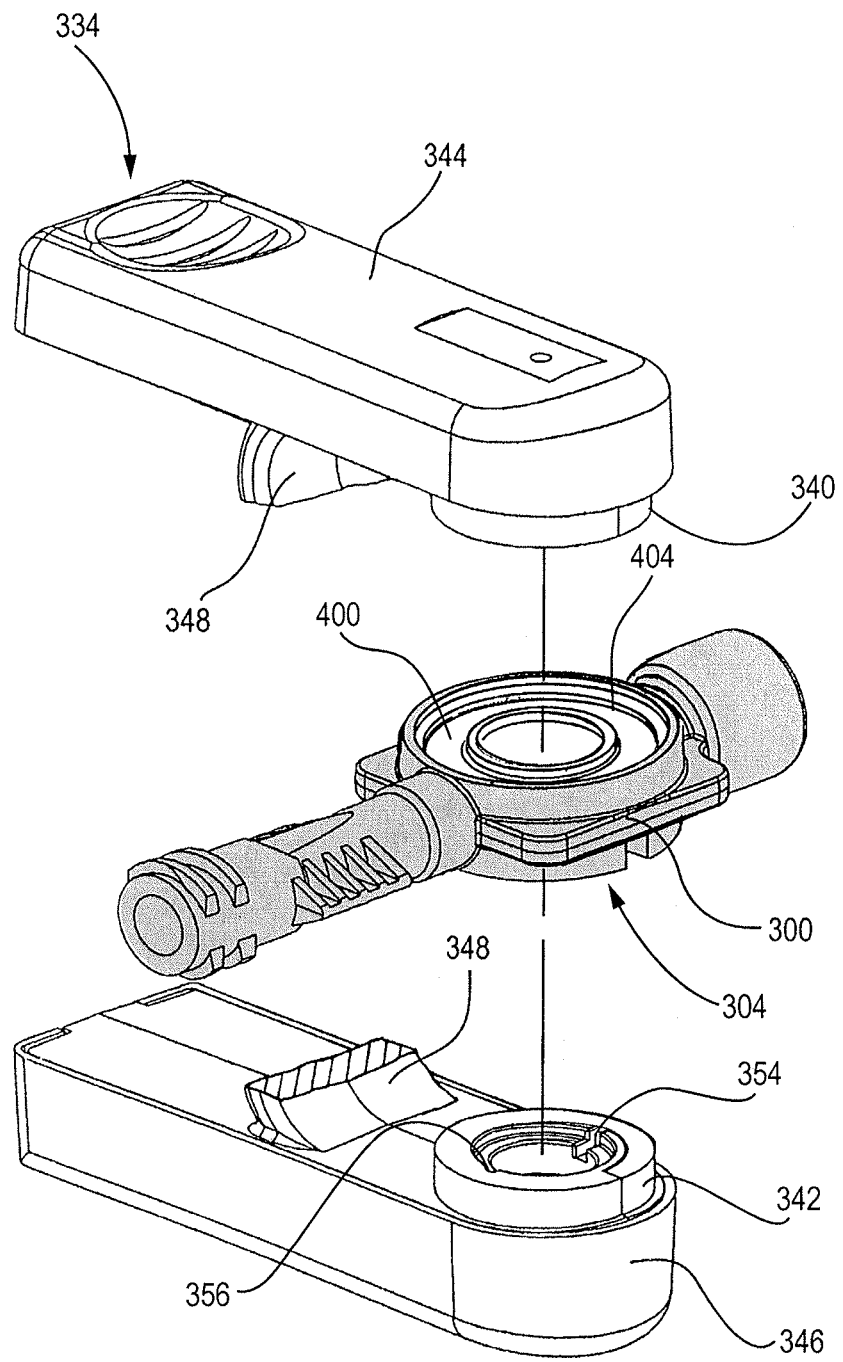
FIG. 20B is the perspective view of the sensor clip assembly and the blood chamber in FIG. 20A with the sensor clip assembly exploded away from the blood chamber to enable a better view of the surfaces of the assembly and chamber that engage when the two are fastened together.

FIG. 19 illustrates a sensor clip assembly 334 configured in accordance with a presently preferred embodiment. The sensor clip assembly 334 is used to monitor the patient's blood flowing through the blood chamber 300. As depicted in the embodiment illustrated in FIG. 20B, the LED emitter arm 344 and the photodetector arm 346 are affixed into place around a blood chamber 300 in order to monitor the hematocrit, hemoglobin, change in blood volume and oxygen saturation level, and/or other blood constituents of blood flowing through the blood chamber 300. Accordingly, the sensor clip assembly 334 preferably includes a spring biased bridge 348 or equivalent structure to attach a sensor clip assembly 334 to a blood chamber 300.

The sensor clip assembly 334 includes an LED emitter arm 344 and a photodetector arm 346, which are connected via a spring biased bridge 348. The LED emitter arm 344 contains an emitter subassembly with at least two LED emitters, one emitting infrared light or radiation at a first wavelength ($\lambda_1$) of about 1300 nm and another emitting infrared light or radiation at a second wavelength ($\lambda_2$) of about 810 nm. The LED emitter preferably also includes a third LED emitter for emitting visible light or radiation at a third wavelength ($\lambda_3$) of about 660 nm. Other wavelengths could be substituted or added to measure additional blood constituents or properties of other fluids. The detector arm 346 contains preferably two types of photodetectors: a silicon photodetector to detect the approximate 660 and 810 nm wavelengths, and an indium gallium arsenide photodetector to detect the approximate 1300 nm wavelength. As configured in the embodiment depicted in FIGS. 19-21, the sensor clip assembly 334 emits infrared light or radiation through the viewing lenses 303 and 400 and through the viewing windows 336 and 338 and through the blood flowing through the flat viewing region 362 of the blood chamber 300 (see FIGS. 21A and 21B).

In contrast to the sensor assembly 34 of FIGS. 2A, 2B, 3B, 4A and 4B, the sensor clip assembly 334 of FIGS. 19, 20A, 20B, 21A and 21B includes two shrouds extending from the heads of the arms 344 and 346 of the assembly. One shroud 340 is on the inner housing piece of the emitter arm 344 subassembly and prevents ambient light from entering the blood chamber through the viewing windows. A second shroud 342 is on the inner housing piece of the detector arm 346 subassembly and also prevents ambient light from entering the blood chamber through the viewing windows.

The shrouds 340 and 342 are preferably mirror images of one another. The description of shroud 340 on the emitter arm 344 therefore is representative and applies equally to the description of the shroud 342 on the detector arm 346. Referring in particular to FIG. 19, it can be seen that shroud 342 contains an outer annular ledge or step surface 350 and an inner annular ledge or step surface 352. The difference in the heights of the step surfaces 350, 352 corresponds to the height of the annular wall 406 on the second exterior side of the blood chamber 300 (see FIG. 15), and also to the height at which the window surface 303 is raised above the sunken well 304 on the first side of the blood chamber 300 (see FIG. 16). Preferably, the shape and surface area of the outer annular step surface 350 is substantially equal to the shape and surface area of the respective shroud mating surfaces 304, 404 on the blood chamber 300, see FIGS. 20A, 20B and 21A, in order to maximize the blocking of ambient light.

Still referring to FIG. 19, the shroud 342 illustrated in FIG. 19 includes slots 354, 356 that are adapted to receive the anti-rotation tabs 307, 308 on the blood chamber 300 (see FIG. 16). The shroud 340 on the emitter arm 344 includes identical slots so that the sensor clip assembly 334 may be clipped on to the blood chamber 300 in either direction. In either direction, however, the sensor clip assembly is fixed in a predetermined position and rotational orientation that assists in eliminating noise that would otherwise likely result from motion artifacts during the factory calibration for the optical monitoring system. This fixed position can be established and maintained in several ways. For example, the shape of the anti-rotation tabs 307, 308 and the corresponding slots 354, 356 may take on any reasonable shape. Also, placing anti-rotation tabs on the shrouds and including mating detents or slots on the blood chamber may be a suitable alternative.

Figure 22:
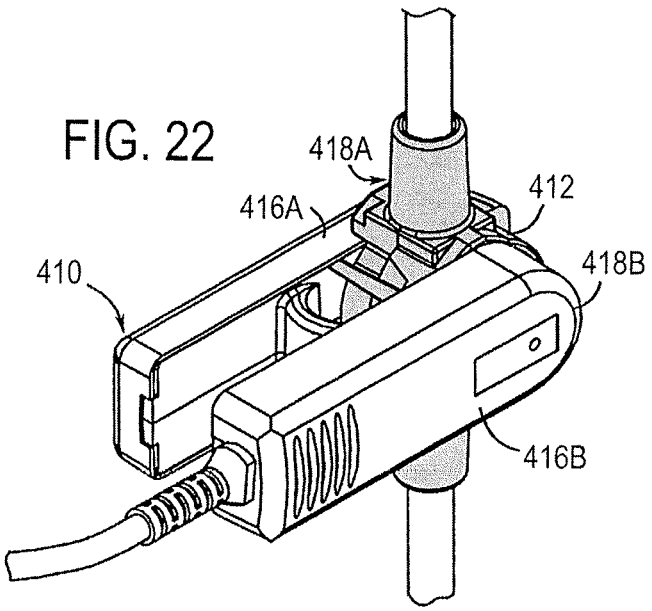
FIG. 22 illustrates an alternative arrangement for fastening the blood chamber to the sensor clip assembly.

One skilled in the art will appreciate that any anti-rotational arrangement for fastening the sensor clip assembly and the blood chamber may be suitable so long as the clip and chamber mate so as to correctly position the LEDs and sensors of the sensor clip assembly with the window of the blood chamber. For example, in co-pending U.S. application Ser. No. 12/876,798, filed Sep. 7, 2010, which is assigned to the same assignee as the present application, the described blood chamber mates with a sensor clip assembly similar to the clip assembly 34 and 334 illustrated herein. FIGS. 1A, 2A and 4A from the '798 application are reproduced herein as FIGS. 22, 23 and 24, respectively, to illustrate an exemplary alternative anti-rotation arrangement. FIG. 22 shows the sensor clip assembly 411 fastened to the blood chamber 412 with the photodetectors on the left hand arm 416A and the photoemitters on the right hand arm 416B. The dimensional characteristics of the left side arm 416A and the right side arm 416B of the sensor assembly 411 are normally congruent, however the blood flow chamber 412 is designed to be used with the photodetectors on either the right hand arm or the left hand arm with the photoemitters being on the opposite side.

Figure 23:
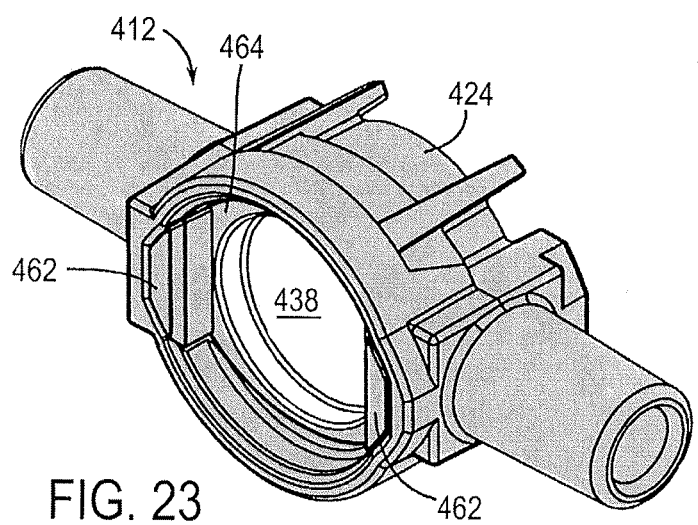
FIG. 23 is a perspective view of the blood chamber in FIG. 22 showing one of the faces of the chamber that mates to an arm of the sensor clip assembly.
Figure 24:
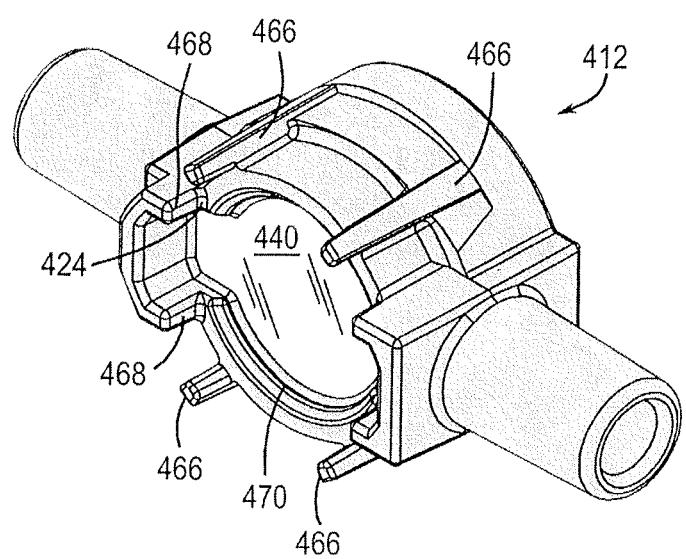
FIG. 24 is a perspective view of the blood chamber in FIG. 22 showing the other face of the chamber that mates with the other arm of the sensor clip assembly.

Referring in particular to FIGS. 23 and 24, the blood chamber 412 includes upstanding pedestals 462 axially disposed along the body 424 of the blood chamber. The pedestals 462 extend outwardly from a sensor receiving wall 464 of the chamber 412. The sensor receiving wall 464 is substantially parallel to a circular lens 438 for the viewing area, and provides an opening for the lens 438 to be exposed to the photoemitters in the head 418A of the sensor clip assembly 411. The pedestals 462 guide the mating arm 416B of the sensor clip assembly 411 into proper rotational alignment when the clip is fastened to the blood chamber 412. This configuration results in the face of the clip arm 418B seating to the blood chamber 412 in proper parallel and rotational orientation with respect to the viewing area for the viewing lens 438.

Referring now in particular to FIG. 24, the other side of the chamber body 424 includes detented receiving ledges 470 surrounding the circular viewing area 440. The chamber body 424 also includes upstanding fingers 466 and guide walls 468 that guide the photodetectors on arm 416B of the sensor clip assembly 411 into proper alignment when the clip sensor assembly is fastened to the blood chamber 412.

Figure 21A:
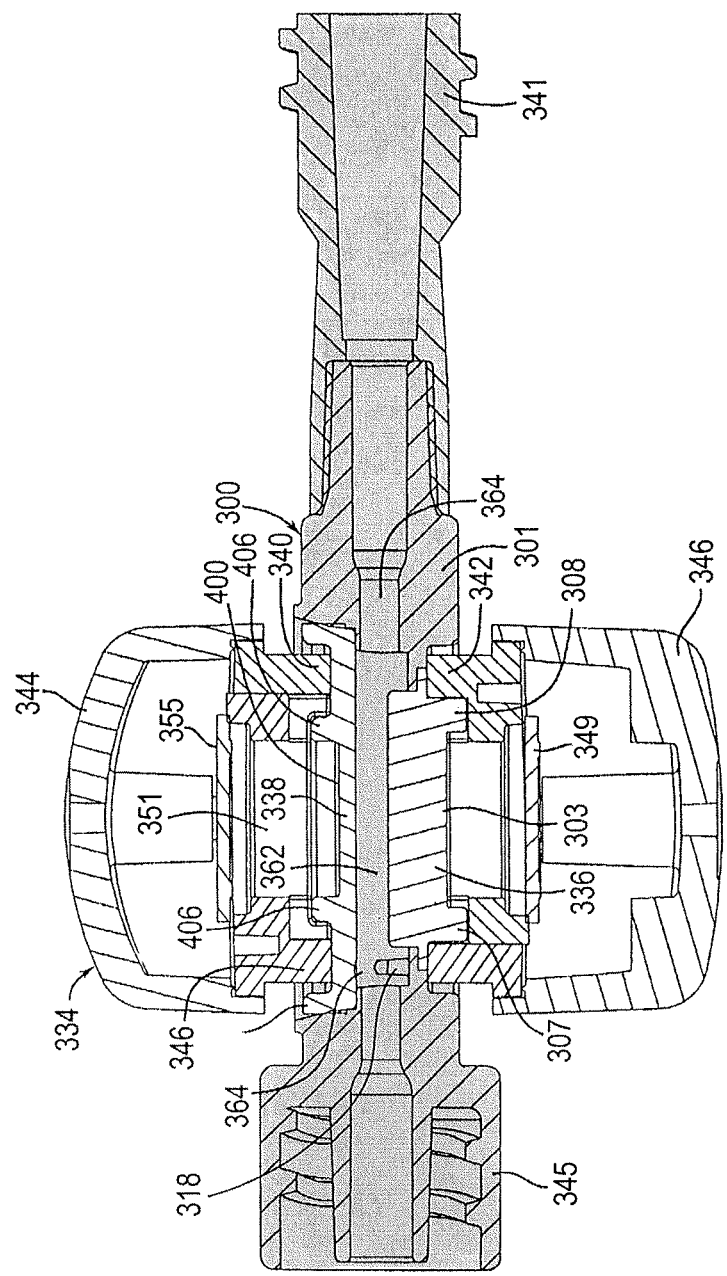
FIG. 21A is a longitudinal, cross-sectional view of the sensor clip assembly fastened to the blood chamber taken along the line 21-21 in FIG. 20A.
Figure 21B:
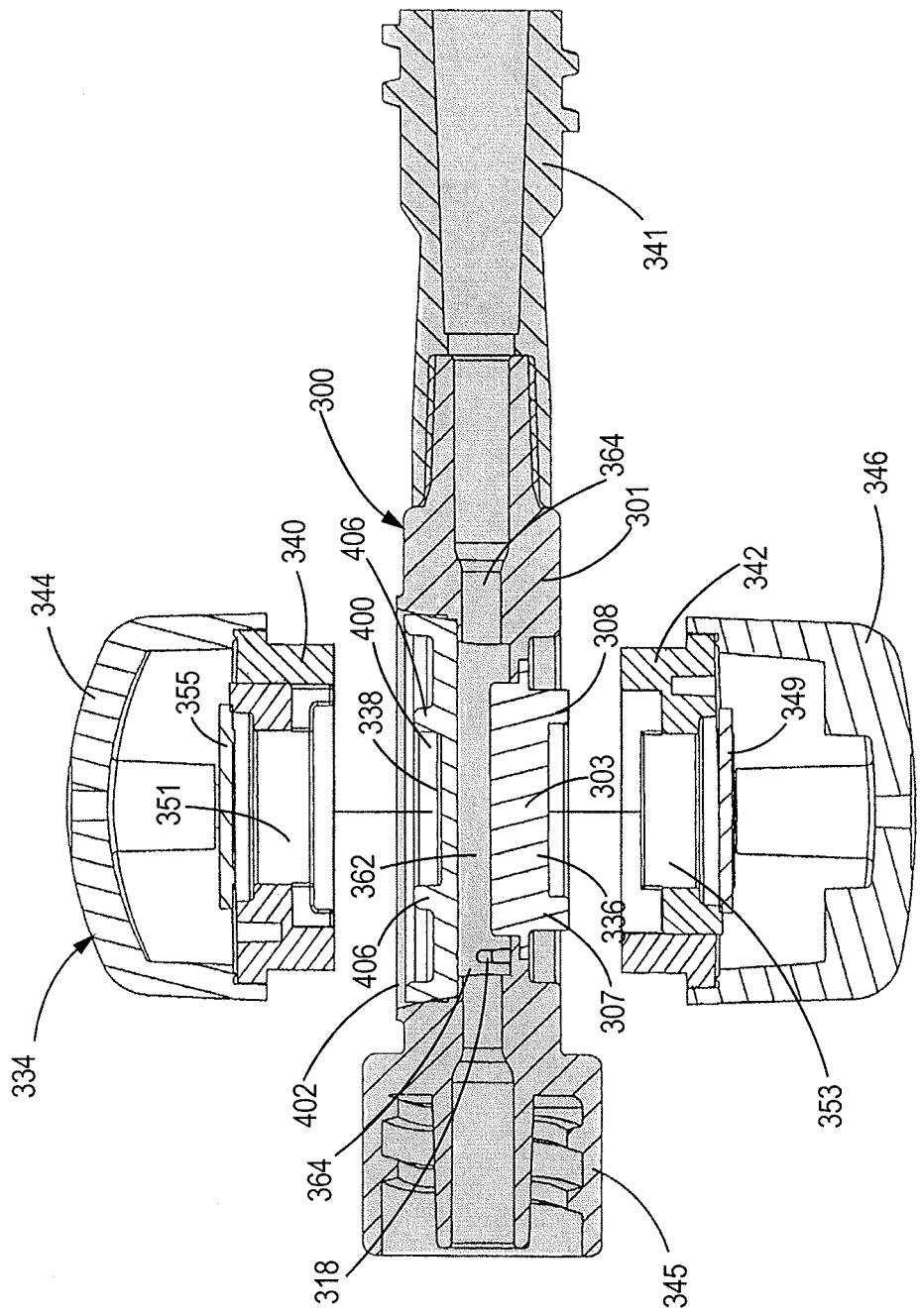
FIG. 21B is the longitudinal sectional view of FIG. 21A with the sensor clip assembly exploded away from the blood chamber.

Returning to FIGS. 21A and 21B, the shrouds at the heads of the arms 344 and 346 of sensor clip assembly 334 are shown in cross section clipped to the blood chamber 300 (FIG. 21A) and exploded away (FIG. 21B) from the chamber. Referring specifically to the blood chamber 300 as shown in FIGS. 21A and 21B, the blood chamber 300 includes two viewing windows 336 and 338. Surface 303 of the first viewing window 336 is exposed on the first exterior side of the blood chamber 300 (see FIG. 16). The exterior surface of the other viewing window 338 is exposed on the other exterior side of the blood chamber 300 (see FIG. 15). The blood chamber 300 includes an inlet 345 and outlet 341 that are designed to be compatible with standard medical industry connecting devices conventionally known as luer lock connectors. In the blood chamber 300 shown in FIGS. 21A and 21B, the inlet 345 is integrally molded with the blood chamber 300, whereas the outlet 341 consists of a suitable off-the-shelf connector adapter bonded to the body of the blood chamber 300. Alternatively, tubing can be attached directly to the body of the blood chamber 300 in place of the connector 341. The LED emitter subassembly 344 as shown in FIGS. 21A and 21B contains an emitter circuit board 355 containing LEDs emitting light at substantially 660 nm, 810 nm and 1300 nm. The LEDs radiate light through the molded diffusing lens 351. As shown in FIGS. 21A and 21B, the shroud 340 on the emitter sub-housing 344 is spaced apart from the molded diffusing lens 351. In addition, the shroud 340 extends towards the detector subassembly 346 beyond diffusing lens 351.

The photodetector subassembly 346 includes a circuit board 349 to which the silicon photodetector, which can detect radiation at 810 nm and 660 nm, and the indium gallium arsenide photodetector, which can detect radiation at 1300 nm, are mounted. The photodetectors are mounted to receive light energy through a molded diffusing lens 353. FIGS. 21A and 21B show that the shroud 342 is spaced apart from the diffusing lens 353 and also that the shroud 342 extends beyond the diffusing lens 353 toward the emitter subassembly 344. In FIGS. 21A and 21B, the anti-rotation tabs 307, 308 are shown in the cross section taken along line 21-21 in FIG. 20A.

The viewing window 336 of the blood chamber 300 in FIGS. 21A and 21B is either part of a separate insert which is then overmolded to the remainder of the chamber body 301 if an opaque body is desired or the window can be molded as part of the chamber body 301 as one piece. The viewing window 338 on the other side of the blood chamber 300 is part of a separately molded insert, which is sonically welded or otherwise adhered to the chamber body. While the windows 303 and 400 should be made of clear material, it is desirable to tint the remaining portions of the chamber body in keeping with the first and second embodiments as described above in order to provide additional protection from unwanted light. Specifically, the blue-tinted polycarbonate material may be used for the remaining portions of the chamber body.

Blood flows from the inlet into the central viewing region of the blood chamber 300 in FIGS. 21A and 21B, which has been referred to previously as the internal blood flow cavity 362. The internal blood flow cavity 362 provides a substantially flat, thin (e.g., less than 0.1 inches) viewing area for the blood flowing through the blood chamber 300. The multiplexed visible or infrared light at the selected wavelengths is transmitted through the blood flowing through the flat viewing region as well as through the viewing windows 336 and 338. A moat 364 surrounds the flat viewing region 362 and provides yet additional protection from unwanted light. The moat 364 is somewhat deeper than the flat viewing region 362, and serves in part to distribute non-laminar flow evenly and steadily through the viewing region. The moat 364 also provides a thicker region of blood which under most operating conditions optically isolates the detectors from unwanted (e.g., ducted or ambient) light that does not pass through the direct path from the photoemitters, through the blood and to the photodetectors.

The viewing windows 303 and 400 are preferably made of clear, medical grade polycarbonate material which is molded with a polished finish in order to facilitate reliable light transmission, e.g., Bayer Makrolon FCR 2458-5515 (no re-grind allowed), which is blood contact approved, USPXX11 class VI. It is expected that the material be certified as to grade number, lot number and date of manufacture. Moreover, the viewing windows should contain no splay, bubbles or marks when looking through the display window viewed from twelve inches with the normal eye. The molded parts should be produced with no lose foreign material greater than 0.1 mm$^2$ and no embedded foreign material greater than 0.2 mm$^2$. No mold release should be used and any lubrications should be food-grade and not silicon-based. The mold finish is preferably SPIA3 (scale) except along the surfaces for the viewing windows, which should preferably be at least SPIA1. Parts should be cleaned and free and dirt, oils and other foreign matter before use.

Fourth Embodiment

FIGS. 25A-29E illustrate a still further embodiment of the blood chamber. The primary difference between the third and the fourth embodiments is the construction of the blood chamber. In this embodiment, the two halves of the main body portion of the blood chamber are made to be mirror images of one another. Likewise, the two opposing lenses welded to the main body portion are constructed to be mirror images of one another. In addition to these features that ease manufacturing of the blood chamber, the lenses are welded to the main body portion of the blood chamber and held in place without the addition of overmolding on the main body portion. The connector affixed to the main body portion is substantially similar to the connector described in association with the previous embodiments.

Figure 25A:
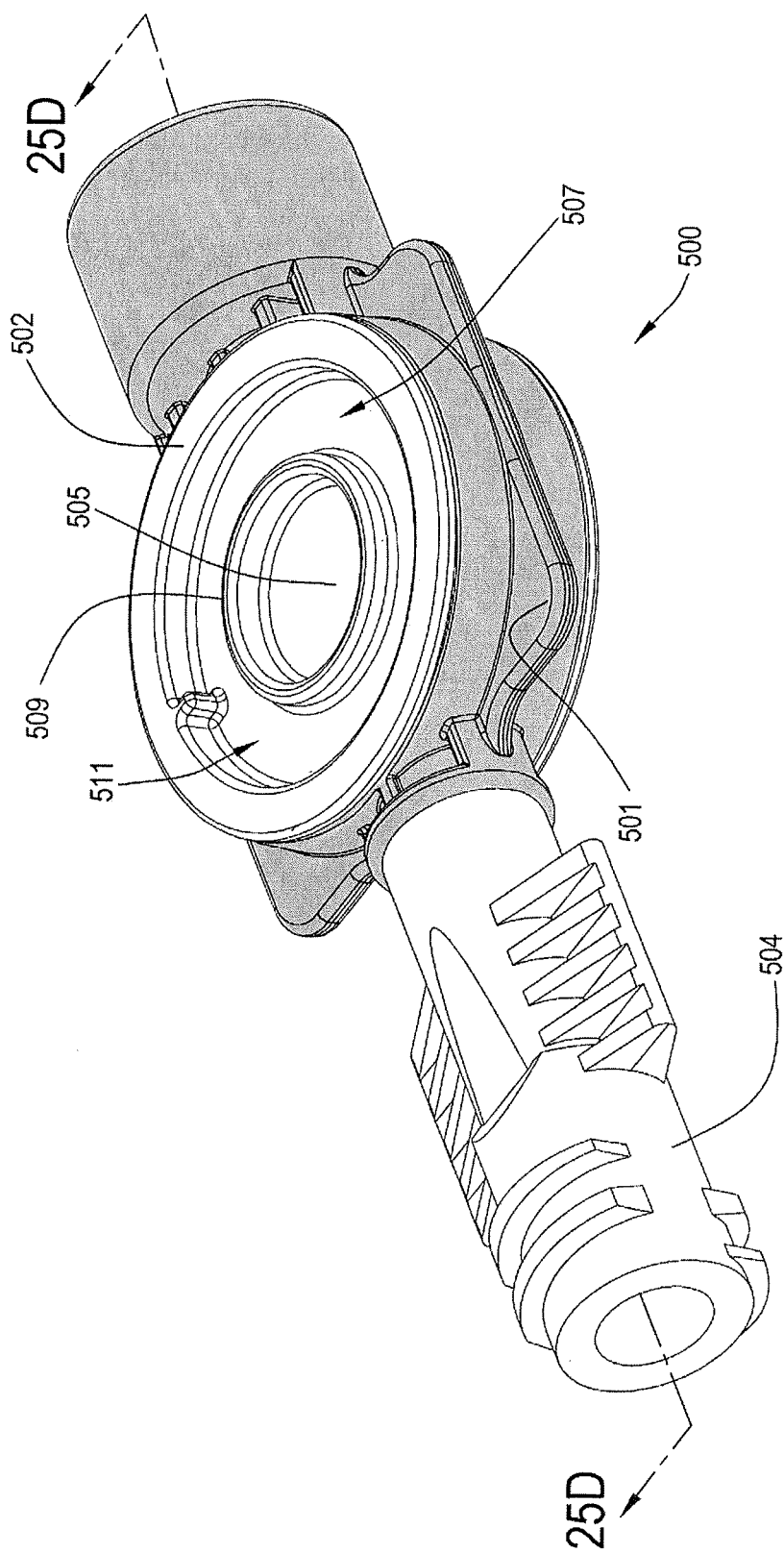
FIG. 25A illustrates a perspective view of a still further alternative embodiment of the blood chamber.

FIG. 25A shows a perspective view of blood chamber 500 of the fourth embodiment. Blood chamber 500 includes main body portion 501, lenses 502, 503, and connector 504. Main body portion 501 is constructed by molding together two mirror image halves. Each half of main body portion 501 has a recess into which lenses 502, 503 can be molded in place. When molded into main body portion 501, lenses 502, 503 are separated by a predetermined distance, and along with main body portion 501 create a blood flow cavity within blood chamber 500.

Lenses 502, 503 may be made entirely of clear, medical-grade polycarbonate material. When lenses 502, 503 are assembled together with main body portion 501, lenses 502, 503 provide each side of the blood chamber 500 with a viewing window 505, 506 into the blood flow cavity. Each lens 502, 503 has a shroud mating surface 507, 508 located circumferentially around viewing windows 505, 506. The shroud mating surfaces 507, 508 are configured to receive the shrouds of the sensor clip assembly. Preferably, when mounted on blood chamber 500, the shrouds on the sensor clip assembly substantially fill shroud mating surfaces 507, 508, thereby maximizing the amount of unwanted light blocked by the shrouds.

Viewing windows 505, 506 are surrounded by upstanding annular walls 509, 510 which separate shroud mating surfaces 507, 508 from viewing windows 505, 506. In this manner, annular wells 511, 512 are formed around viewing windows 505, 506 that are at substantially the same depth as the viewing window. Annular wells 511, 512 are congruent to shroud mating surfaces 507, 508 on the exterior sides of blood chamber 500.

Figure 25B:
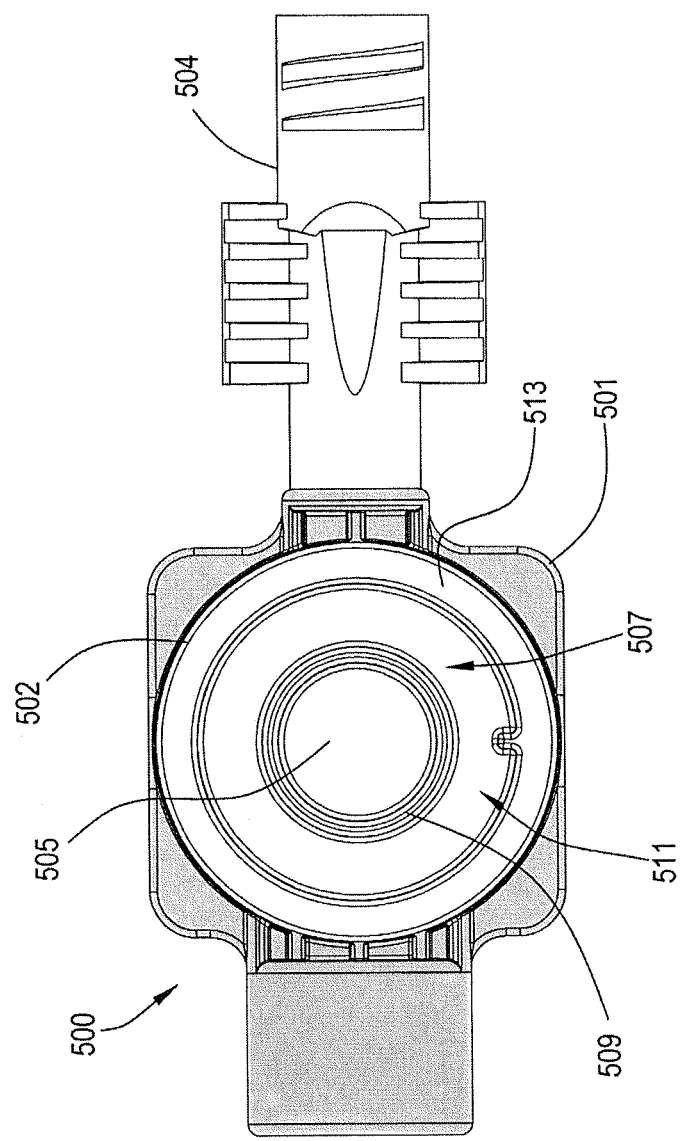
FIG. 25B is a top elevation view of the blood chamber of FIG. 25A.

FIG. 25B illustrates one exterior side of blood chamber 500. Because the sides of blood chamber 500 are mirror images of each other, only one side of blood chamber 500 will be discussed in detail. Blood chamber 500 is constructed from a main body portion 501 which includes an inlet and an outlet. Main body portion 501 may be molded entirely of clear, medical-grade polycarbonate material or other suitable material. Alternatively, it may be desirable to mold main body portion 501 with an opaque material such as the blue-tinted medical-grade polycarbonate material of the previous embodiments.

In either case, main body portion 501 includes lenses 502, 503, each of which has a circular viewing window 505, 506. In operation, blood flows through the internal blood flow cavity defined by lenses 502, 503 and main body portion 501 within blood chamber 500. Lenses 502, 503, including their circular viewing window portions 505, 506, are made of a material such as clear, medical-grade polycarbonate. Viewing windows 505, 506 thus provide an optically neutral view for the sensor clip assembly to monitor the blood flowing through blood chamber 500. As shown in FIG. 29B, upstanding annular wall 509 surrounds viewing window 505. Lenses 502, 503 each also have peripheral walls 513, 514 that are concentric with upstanding annular walls 509, 510, and positioned at the periphery of lenses 502, 503. In this manner, annular wells 511, 512 are defined by annular walls 509, 510 and peripheral walls 513, 514. The floor of annular well 511 is another shroud mating surface 507 which is separate and distinct from viewing window 505. In accordance with the presently preferred embodiment, lens 502 containing viewing window 505, upstanding annular wall 509, peripheral wall 513, and annular well 511, is molded from a clear polycarbonate material and is attached via sonic welding or other means to main body portion 501 during the manufacturing process. Lens 503, with its associated components, is manufactured from the same material and attached to main body portion 501 in the same fashion as lens 502.

Figure 25C:
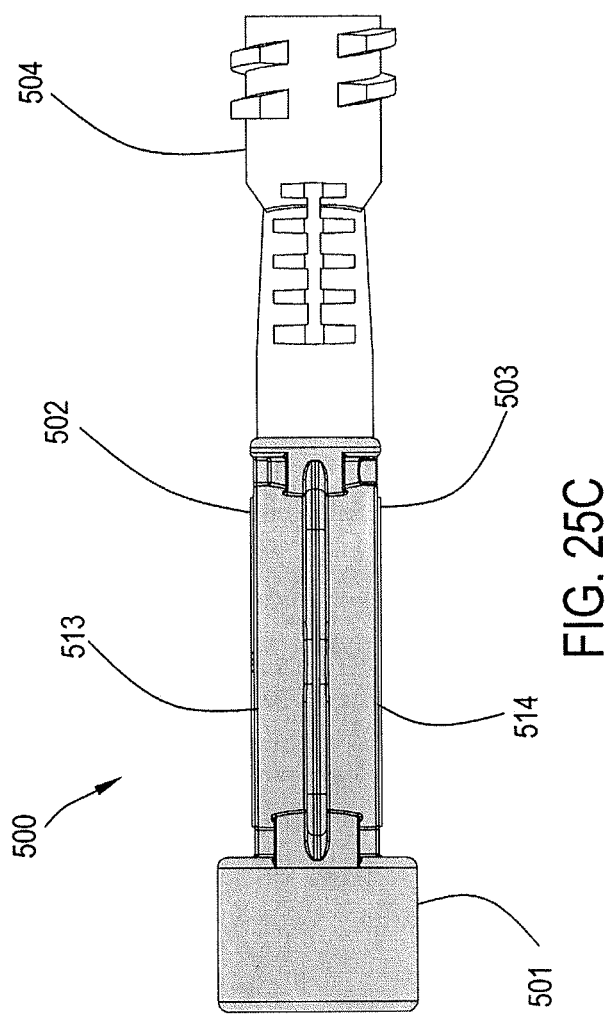
FIG. 25C is a side elevation view of the blood chamber of FIG. 25A.

FIG. 25C illustrates a side elevation of blood chamber 500. Main body portion 501 is connected to connector 504. Connector 504 may be a luer lock connector, such as the connectors previously described herein. Main body portion 501 is fitted with lenses 502, 503 on opposing sides of main body portion 501. Peripheral walls 513, 514 of lenses 502, 503 are visible from the side elevation view of blood chamber 500. The internal blood flow cavity is defined by the predetermined distance between lenses 502, 503 when they are molded to main body portion 501, and is bounded around its circumference by main body portion 501.

Figure 25D:
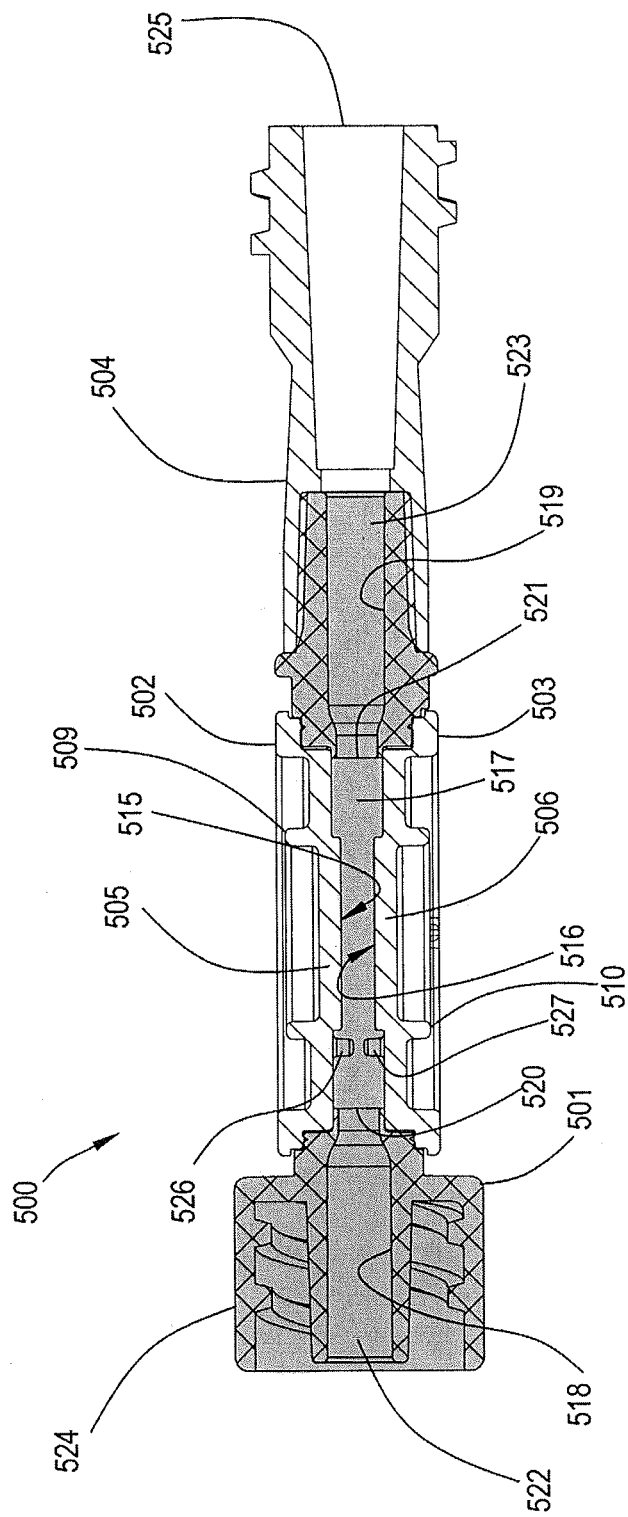
FIG. 25D is a longitudinal cross-sectional view of the blood chamber of FIG. 25A.

FIG. 25D shows the cross section of blood chamber 500. Lenses 502, 503 are attached to main body portion 501, and include substantially flat internal walls 515, 516 that form part of blood flow cavity 517. Internal wall 515 is substantially parallel to internal wall 516, and separated therefrom by a predetermined fixed distance. Viewing windows 505, 506 allow observance of the blood flowing through internal blood flow cavity 517.

Main body portion 501 includes a first port 518 and a second port 519. Blood flow cavity 517 includes a first opening 520 and a second opening 521. First port 518 and first opening 520 are in fluid communication through first channel 522. Second port 519 and second opening 521 are in fluid communication through second channel 523. Blood chamber 500 also includes inlet 524 and outlet 525. In a preferred embodiment, blood flows into inlet 524, through first channel 522, and into blood flow cavity 517 where its characteristics are sensed by the sensor clip assembly. After passing through blood flow cavity 517, the blood passes through second channel 523, and exits blood chamber 500 from outlet 525.

As best seen in FIG. 25D, lenses 502, 503 each include a pair of turbulence posts. Pairs of turbulence posts 526, 527 are integral to lenses 502, 503. Lenses 502, 503 are molded to main body portion 501 such that pairs of turbulence posts 526, 527 are positioned near first opening 520 of blood flow cavity 517. As with the posts of previous embodiments, pairs of turbulence posts 526, 527 provide resistance to suppress any tendency of the blood to flow a purely laminar fashion, which if not suppressed, may result in the blood not filling blood flow cavity 517. Pairs of posts 526, 527 also create eddy currents within the blood in blood flow cavity 517, which tend to mix the blood to a more homogenous consistency that provides for better measurements by the sensor clip assembly. Because either first port 518 or second port 519 could serve as an inlet port, as explained in connection with the first and second embodiments, pairs of posts 526, 527 can be on either end of blood flow cavity 517 depending on the molding orientation of lenses 502, 503 with respect to main body portion 501. Turbulence posts positioned at the blood flow's entrance into blood flow cavity 517 ensure that the posts properly provide resistance to break up a laminar flow and to create eddy currents to mix the blood before its characteristics are sensed.

Figure 25E:
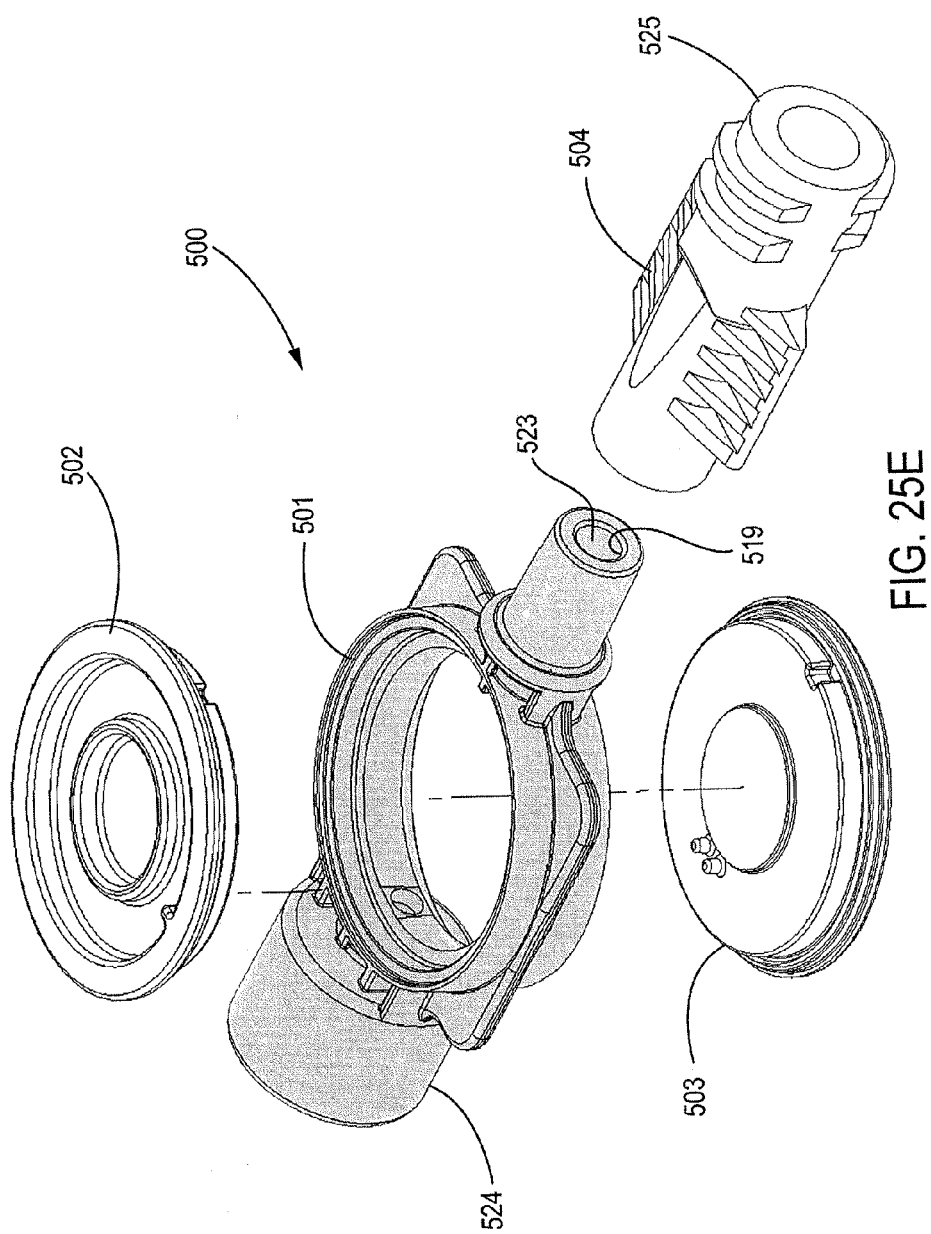
FIG. 25E is an exploded perspective view of the blood chamber of FIG. 25A.

FIG. 25E shows an exploded view of the components of the fourth embodiment of blood chamber 500. During the manufacturing process, lenses 502, 503 are received in and attached to main body portion 501, creating internal blood flow cavity 517 of blood chamber 500. Lenses 502, 503 are mirror images of each other. When lenses 502, 503 are attached to main body portion 501, they are positioned such that they are substantially parallel and opposite each other. Connector 504 may be attached to main body portion 501 at the second port 519 of main body portion 501. In this manner, blood flowing from internal blood flow cavity 517 passes out of second port 519 through second channel 523, through connector 504, and out of outlet 525. After the blood flows from outlet 525, it may flow to a dialyzer or blood filter, such as dialyzer or blood filter 22 shown in FIG. 1.

Figure 26A:
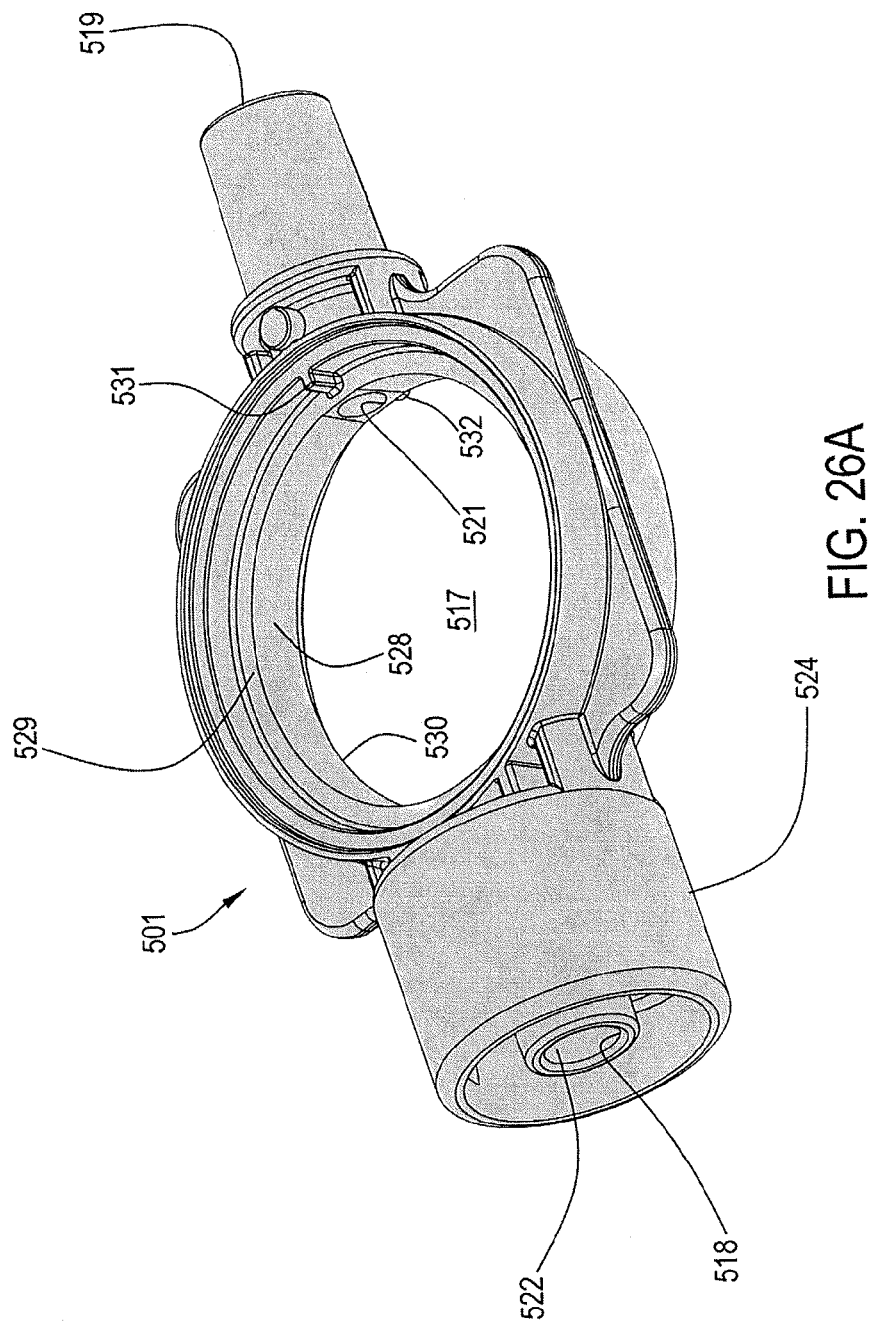
FIG. 26A is a perspective view of the main body portion of the blood chamber of FIGS. 25A-E.
Figure 26B:
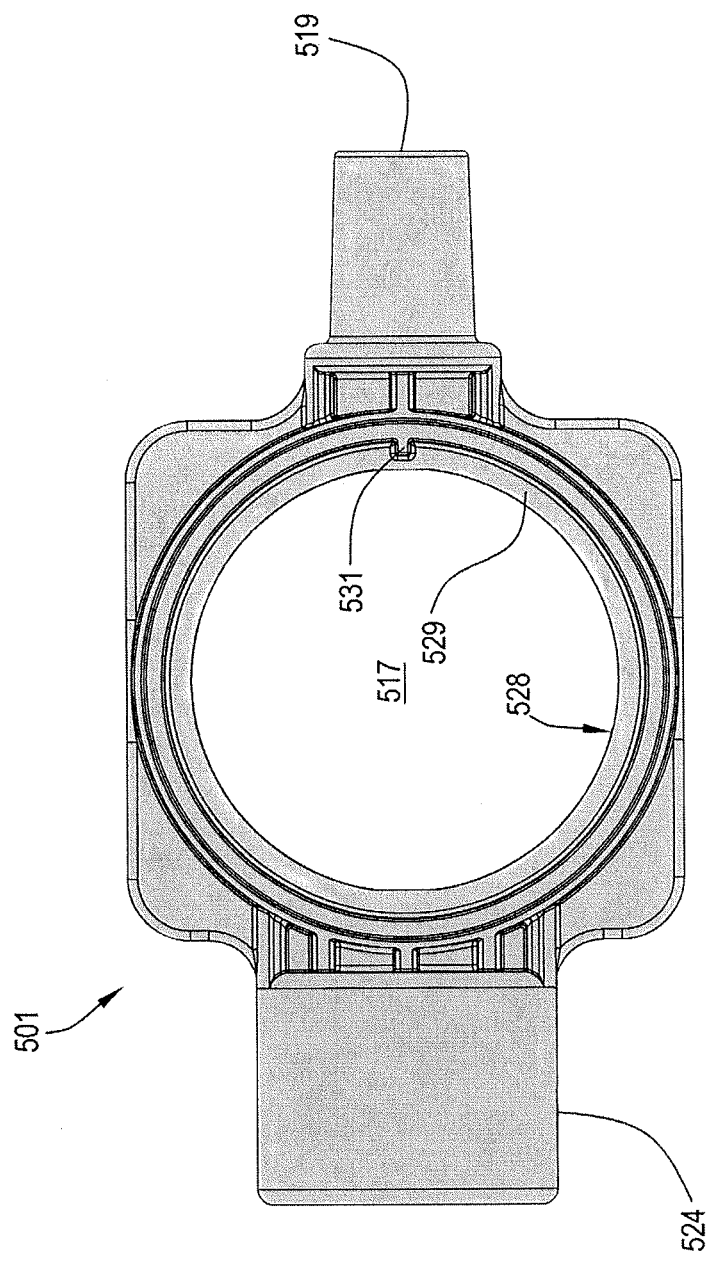
FIG. 26B is a top elevation view of the main body portion of the blood chamber of FIG. 26A.

FIGS. 26A-B illustrate main body portion 501 of blood chamber 500 in its simplest form, where the two molded halves of the body are mated, but the connector and lenses have not yet been added. As shown in FIG. 26A, sidewall 528 extends in a substantially circular manner around an inner periphery of main body portion 501. Extending substantially orthogonally from sidewall 528 are receiving ledges 529, 530. Receiving ledges 529, 530 are also substantially circular. During assembly, lenses 502, 503 are received in main body portion 501 on receiving ledges 529, 530. To properly orient lenses 502, 503 with respect to main body portion 501, main body portion 501 includes protrusions 531, 532 located on receiving ledges 529, 530, adjacent sidewall 528. In the illustrated embodiment, protrusions 531, 532 are located on opposite sides of sidewall 528, and positioned in line with second opening 521. Lenses 502, 503 are positioned with respect to main body portion 501 so that protrusions 531, 532 are received in complementary recesses on lenses 502, 503. When paired in this manner, lenses 502, 503 become seated on receiving ledges 529, 530, and internal walls 515, 516 of lenses 502, 503, together with sidewall 528, define blood flow cavity 517. Specifically, sidewall 528 extends between flat internal walls 515, 516 when lenses 502, 503 are mated to main body portion 501. Although the illustrated embodiment uses generally cubical protrusions and recesses, the protrusions and recesses may take on any reasonable geometric shape. Furthermore, other types of fasteners or rotational stops may work equally well and are contemplated.

Main body portion 501 includes inlet 524, which houses first port 518. First channel 522 passes through first port 518. First port 518 and first channel 522 are in fluid communication with internal blood flow cavity 517 through first opening 520 in sidewall 528. Main body portion 501 also includes second port 519. Second channel 523 passes through second port 519. Second port 519 and second channel 523 are in fluid communication with internal blood flow cavity 517 through second opening 521 in sidewall 528. In the embodiment shown in FIGS. 26A-B, second port 519 and second channel 523 are in axial alignment with first port 518 and first channel 522 along an axis that spans across the middle of internal blood flow cavity 517.

FIG. 26B shows a top elevation view of main body portion 501. During assembly, lens 502 (not shown) is received on receiving ledge 529 and the complementary recess on lens 502 is aligned with protrusion 531, forming one boundary of blood flow cavity 517. In the illustrated embodiment, inlet 524 is opposite second port 519 on main body portion 501. Inlet 524 is also in axial alignment with second port 519 along an axis that spans across the middle of internal blood flow cavity 517.

Figure 27A:
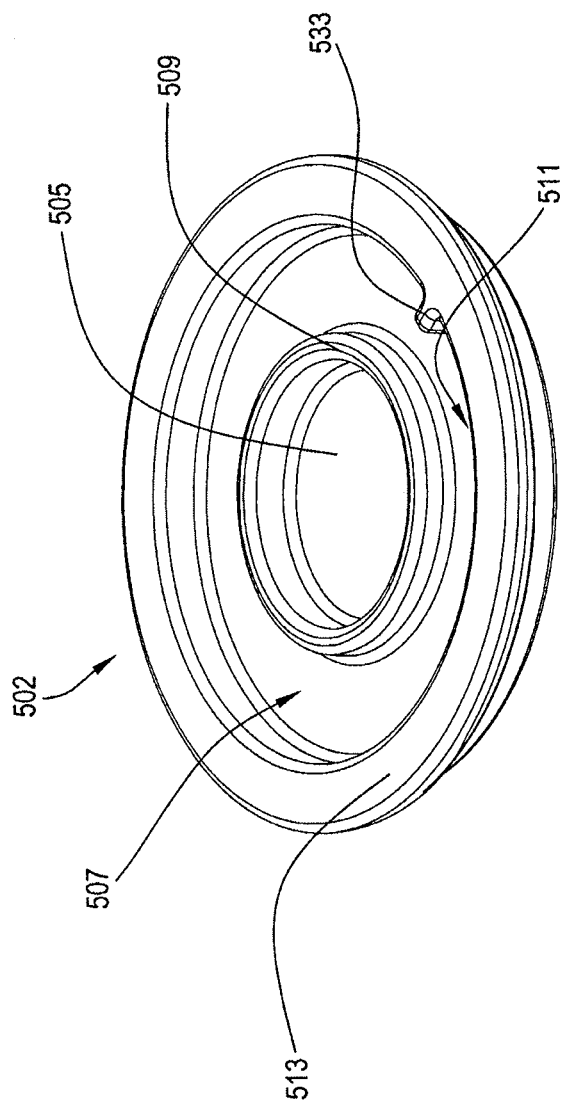
FIG. 27A is a perspective view of one of the two opposing lenses of the blood chamber of FIGS. 25A-E.
Figure 27B:
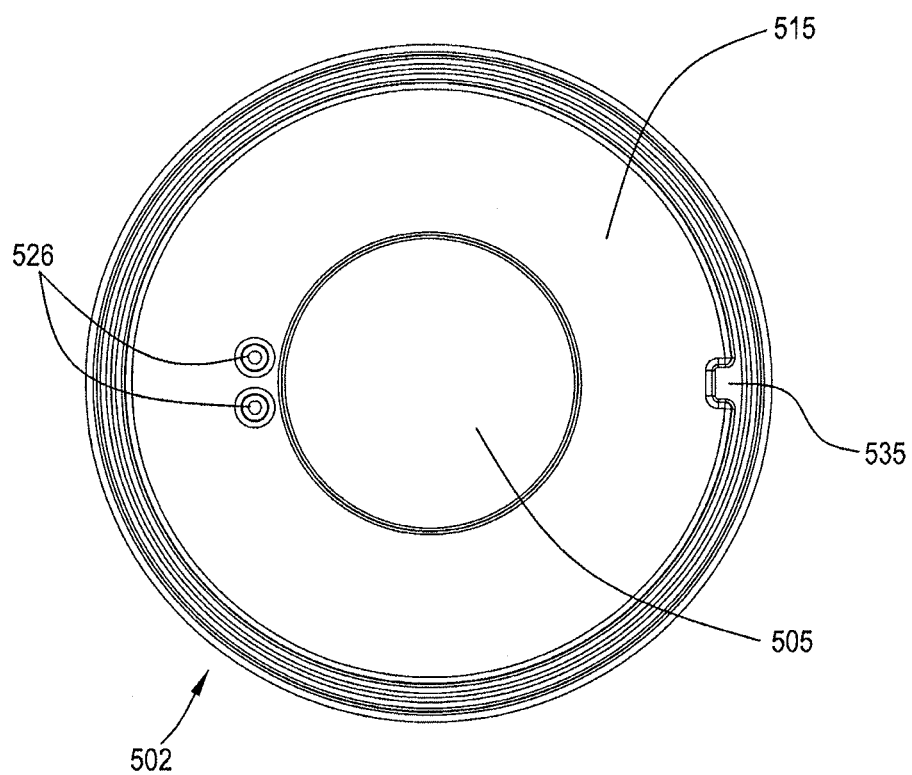
FIG. 27B is a bottom elevation view of the lens of FIG. 27A.

FIGS. 27A-B show perspective and bottom elevation views of one of the lenses of blood chamber 500 by itself. Because lenses 502, 503 are mirror images of each other, only lens 502 will be discussed in detail. FIG. 27A shows lens 502 with viewing window 505 at its center. Lens 502 includes two concentric rings of ridges. The inner ring is upstanding annular wall 509, and it surrounds viewing window 505. The outer ring is peripheral wall 513 and it is situated at the periphery of lens 502 near where the lens mates to main body portion 501. The area between annular wall 509 and peripheral wall 513 defines annular well 511. The floor of annular well 511 is shroud mating surface 507, which is separate and distinct from viewing window 505 and configured to receive the shroud of one arm of the sensor clip assembly.

When mated, annular well 511 and the spring bias of the clip assembly hold the clip and blood chamber 500 together. To prevent relative rotation of the clip and blood chamber 500, lens 502 includes anti-rotation tab 533 that extends radially inward from peripheral wall 513. Lens 503 has a corresponding anti-rotation tab 534. Anti-rotation tabs 533, 534 are positioned on the sides of lenses 502, 503 that are opposite internal walls 515, 516. That is, when lenses 502, 503 are received in main body portion 501, anti-rotation tabs 533, 534 face outward from the exterior sides of blood chamber 500. In this orientation, anti-rotation tabs 533, 534 mate to receiving slots in the shrouds of the sensor clip assembly, rotationally locking the mated clip assembly and blood chamber 500.

The anti-rotation tabs 533, 534 of lenses 502, 503 and the complementary receiving slots on the shrouds of the sensor clip assembly may take on any reasonable geometric shape. Furthermore, other types of fasteners or rotational stops may work equally well and are contemplated. For example, either the lenses or the clip can include alignment posts that guide the blood chamber and clip into proper engagement to both register the LEDs and photodetectors with the lenses and to prevent rotation. The interaction between anti-rotation tabs 533, 534 and the receiving slots on the shrouds of the sensor clip assembly will be described further below.

FIG. 27B illustrates pair of turbulence posts 526 on lens 502 that extend into blood flow cavity 517 and introduce turbulence into the blood flow. Without posts 526, the blood flow through blood flow cavity 517 of blood chamber 500 is more susceptible to a laminar flow that reduces the quality of the measurements by the detectors in the clip assembly. Also shown in FIG. 27B is complementary recess 535 of lens 502. Complementary recess 535 is configured to mate with protrusion 531 that sits on receiving ledge 529 of main body portion 501 (see FIGS. 26A-B). The protrusion-recess interaction helps ensure that lenses 502, 503 are properly oriented with respect to main body portion 501 during assembly of the blood chamber 500. When complementary recess 535 is positioned substantially in line with and opposite turbulence posts 526, as shown on lens 502, turbulence posts 526 are in near proximity to first opening 520 of main body portion 501. Locating turbulence posts 526 near first opening 520 and the entrance of blood flow cavity 517 causes turbulence posts 526 to disturb the laminar flow of blood entering the blood flow cavity of blood chamber 500.

Figure 28A:
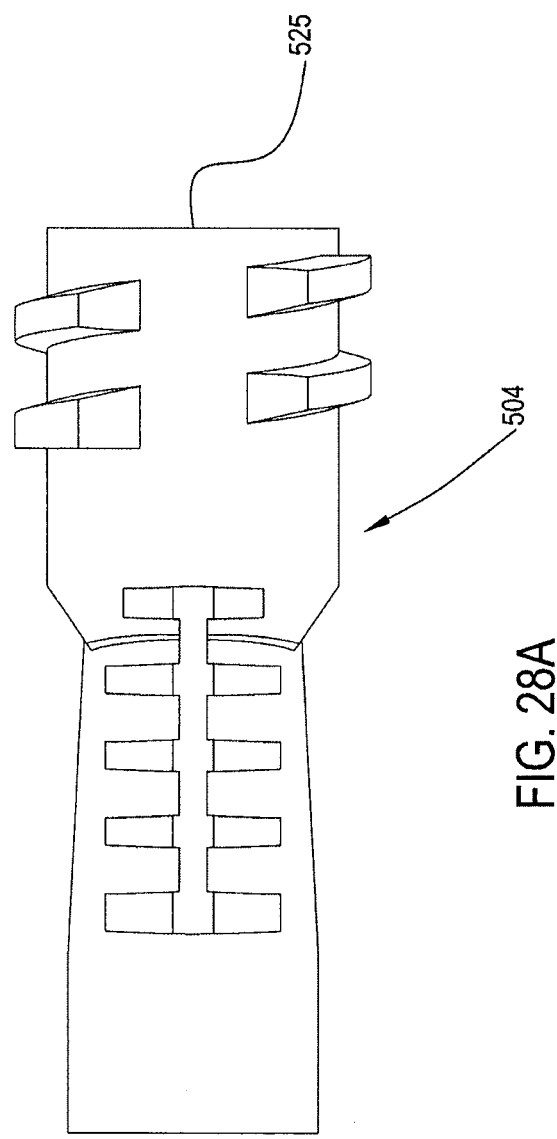
FIG. 28A is a side elevation view of the connector of the blood chamber of FIGS. 25A-E.
Figure 28B:
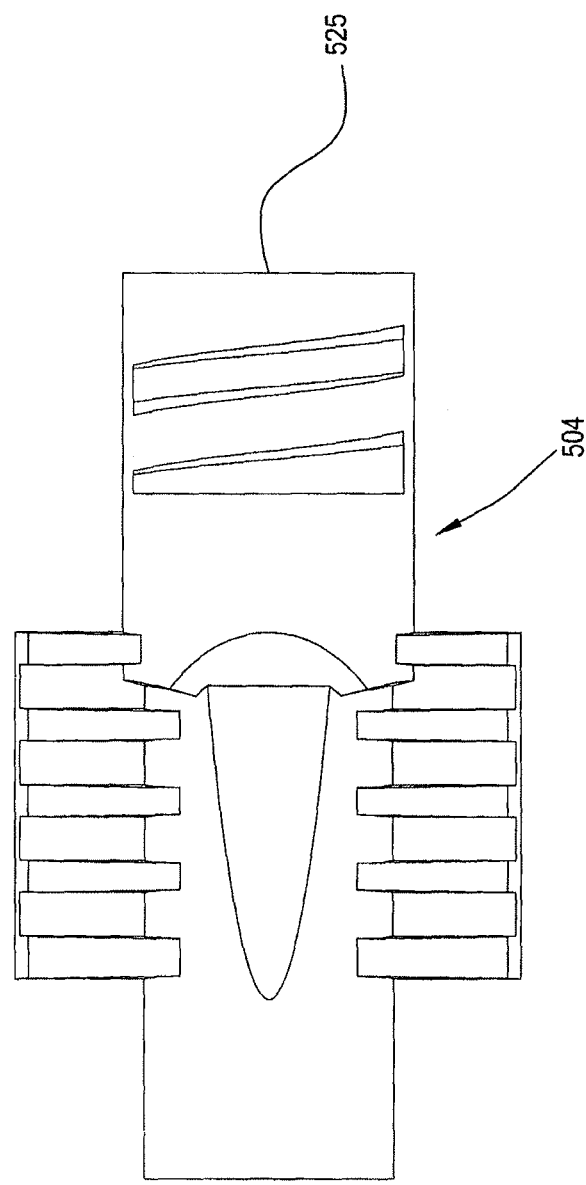
FIG. 28B is a top elevation view of the connector of FIG. 28A.

FIGS. 28A-B are views of connector 504 in isolation. In the blood chamber of the fourth embodiment, inlet 524 (see FIG. 25D) and outlet 525 of connector 504 are designed to be compatible with standard medical industry connecting devices, conventionally known as luer lock connectors.

FIGS. 29A-E illustrate a sensor clip assembly configured in accordance with a presently preferred embodiment. The blood chamber of this embodiment fits with the sensor clip assembly in substantially the same way as described above in connection with the third illustrated embodiment. When the sensor clip assembly is mated to the blood chamber, the shrouds of the sensor clip assembly block unwanted light from the viewing windows of the blood chamber.

Figure 29A:
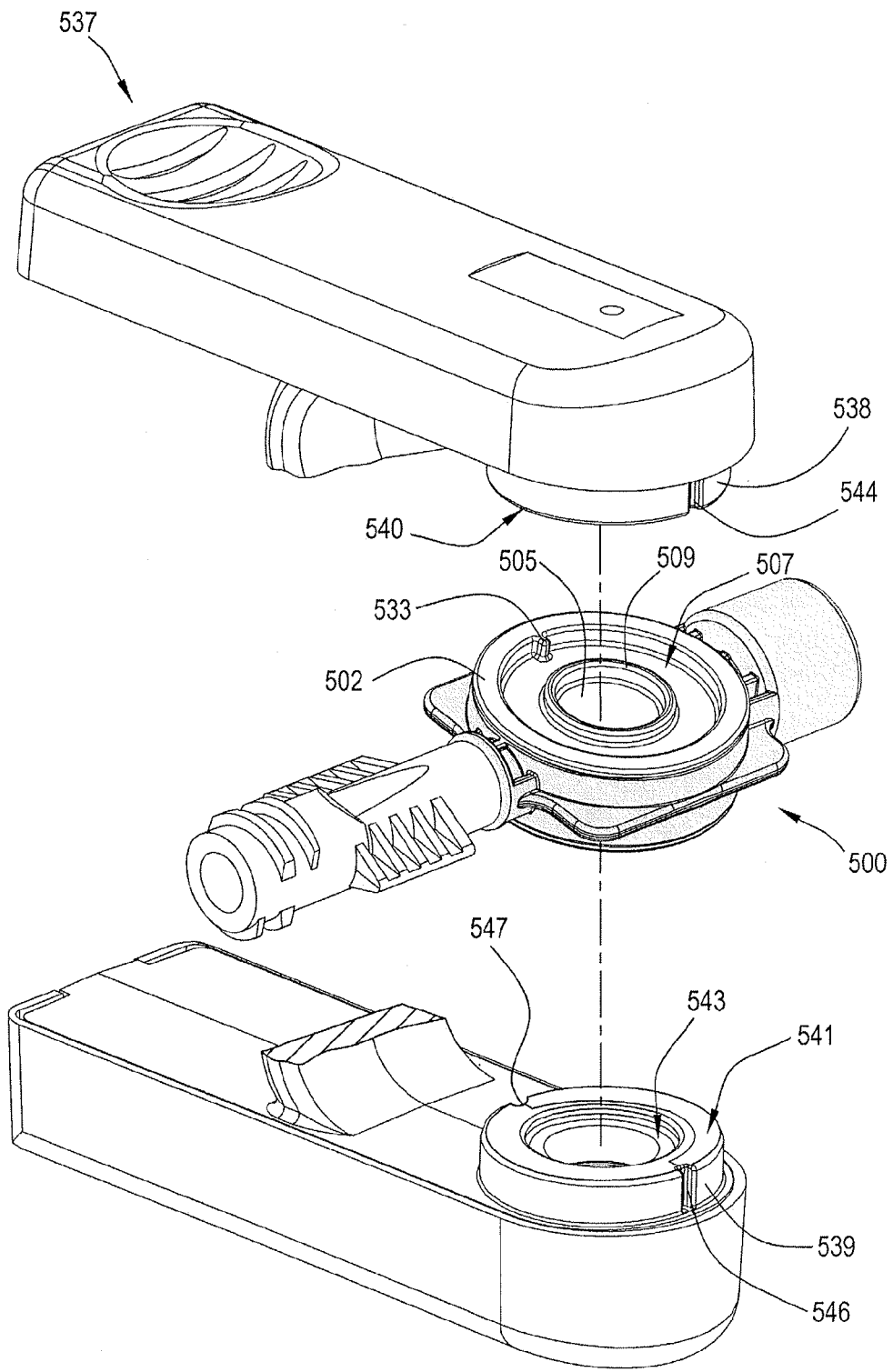
FIG. 29A is an exploded perspective view of the sensor clip assembly and the blood chamber of FIGS. 25A-E.
Figure 29B:
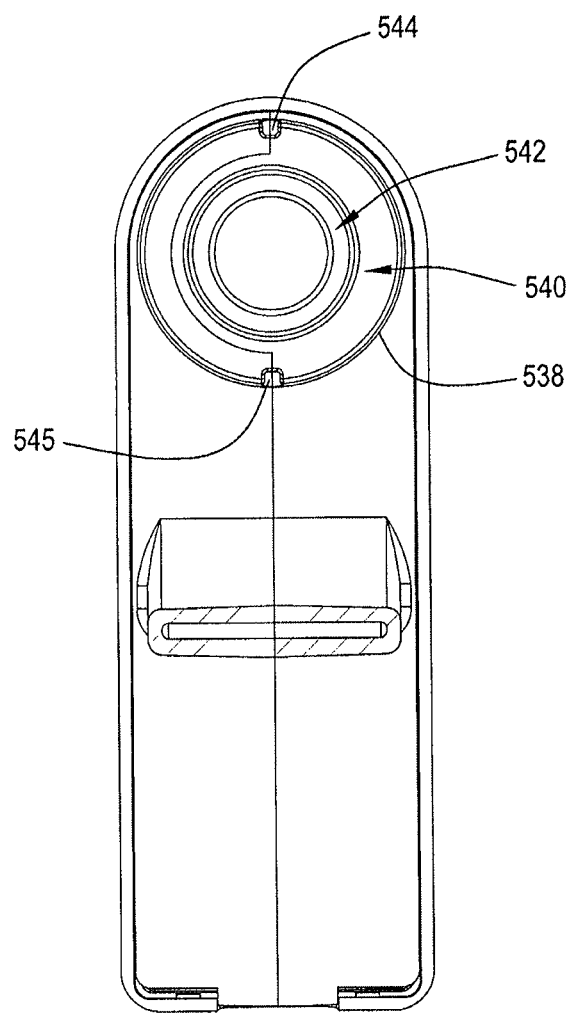
FIG. 29B is an elevation view of the shroud-mating surface of one arm of the sensor clip assembly of FIG. 29A.

FIG. 29A shows sensor clip assembly 537 exploded away from blood chamber 500. Shrouds 538 and 539 are mirror images of one another, and attached to both arms of sensor clip assembly 537 at the heads of the arms. Shrouds 538, 539 each include an outer annular ledge 540, 541, and an inner annular ledge 542, 543. The difference in the heights of the outer and inner annular ledges corresponds to the height of annular walls 509, 510 on lenses 502, 503. Preferably, the shape and surface area of outer annular ledges 540, 541 are substantially similar to the shape and surface area of the respective shroud mating surfaces 507, 508 on lenses 502, 503 in order to maximize the blocking of ambient light.

As shown in FIG. 29A, and more particularly in the front elevation view of one arm of the sensor clip assembly in FIG. 29B, shrouds 538, 539 each include a pair of receiving slots. In particular, shroud 538 includes receiving slots 544, 545, and shroud 539 includes receiving slots 546, 547. In the illustrated embodiment, and on each shroud, the two receiving slots are diametrically opposed from each other and are positioned on outer annular ledges 540, 541. Receiving slots 544, 545 and 546, 547 are adapted to receive anti-rotation tabs 533, 534 that are integral to lenses 502, 503 of blood chamber 500. Depending on the orientation of blood chamber 500 with respect to sensor clip assembly 537, anti-rotation tab 533 may be received in receiving slot 544 or in receiving slot 545, and anti-rotation tab 534 may be received in receiving slot 546 or in receiving slot 547.

When the shrouds and their receiving slots are configured in this manner, sensor clip assembly 537 may be fixed in a predetermined positional and rotational orientation with respect to blood chamber 500 that assists in eliminating noise that would otherwise likely result from motion artifacts during the factory calibration of the optical monitoring system. The fixed position can be established and maintained in other ways, including those previously described in connection with other embodiments. For example, the shapes of anti-rotation tabs 533, 534 and corresponding receiving slots 544, 545 and 546, 547 may take on any reasonable configuration. Also, placing anti-rotation tabs on the shrouds and including mating detents or receiving slots on the blood chamber may be a suitable alternative.

Figure 29C:
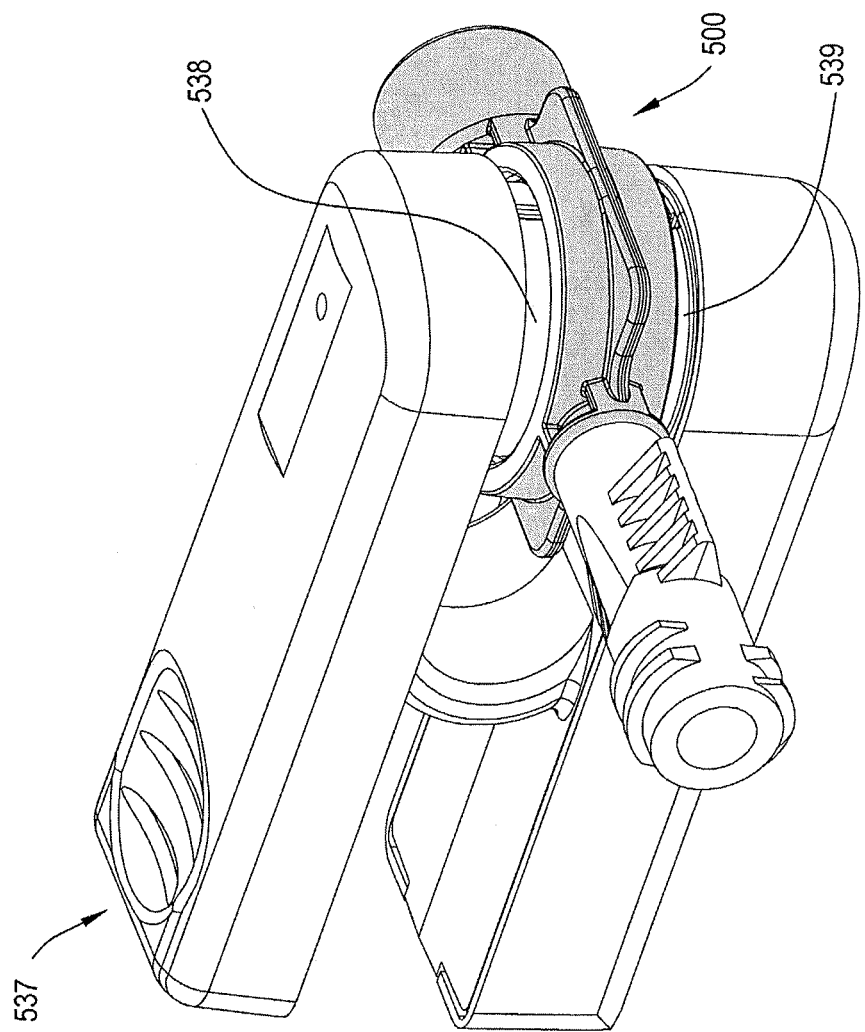
FIG. 29C is a perspective view of the sensor clip assembly attached to the blood chamber of FIGS. 25A-E.

FIG. 29C shows sensor clip assembly 537 attached to blood chamber 500. In the illustrated embodiment, sensor clip assembly 537 is oriented at a substantially right angle with respect to blood chamber 500 due to the relative positions of anti-rotation tabs 533, 534 on lenses 502, 503 and receiving slots 544, 545 and 546, 547 on shrouds 538, 539. It is contemplated that the relative position of the anti-rotation tabs and receiving slots could be different than that shown, producing a different relative angle between sensor clip assembly 537 and blood chamber 500.

Figure 29D:
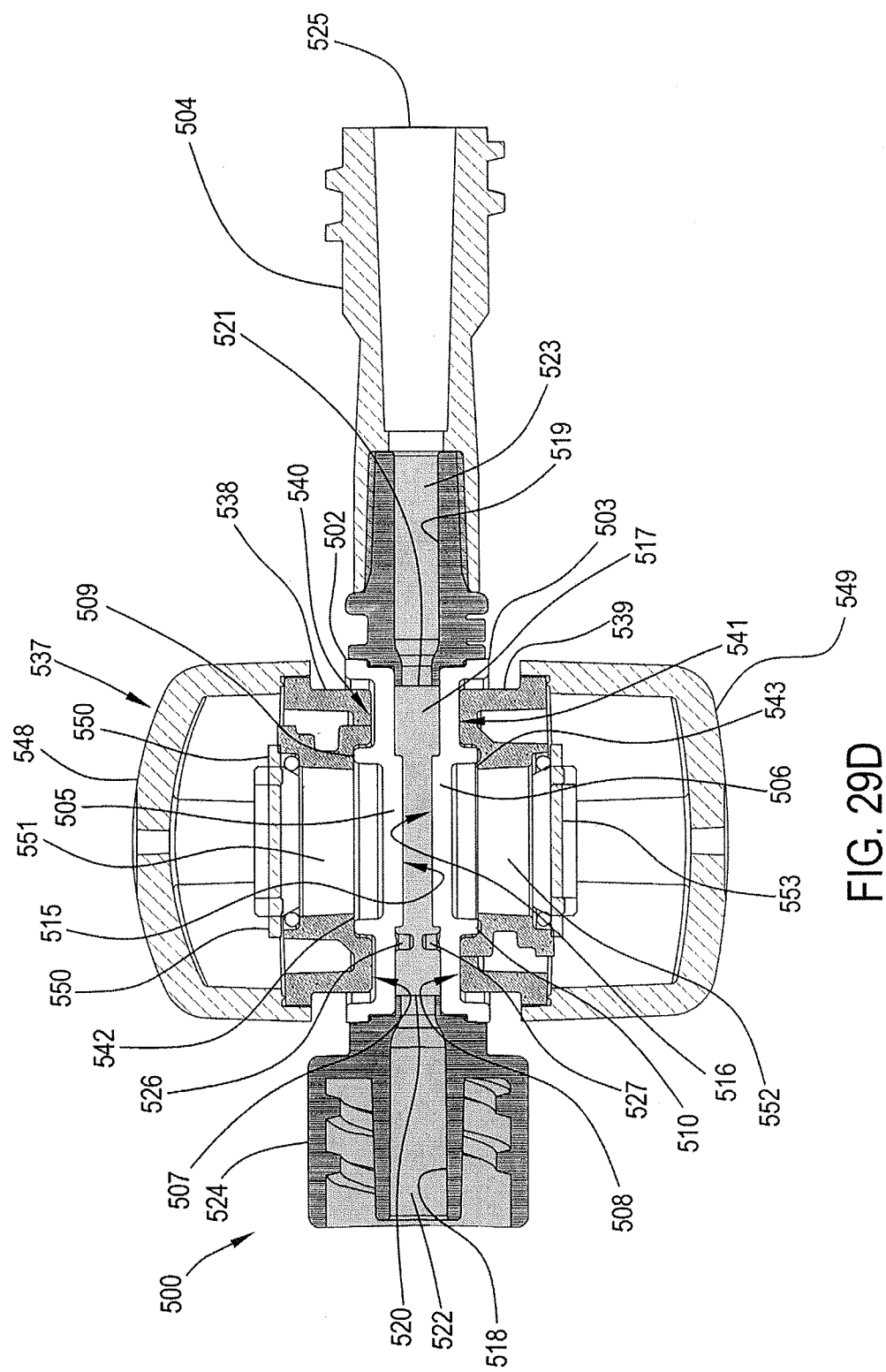
FIG. 29D is a longitudinal cross-sectional view of the blood chamber of FIGS. 25A-E when attached to the sensor clip assembly of FIG. 29A.
Figure 29E:
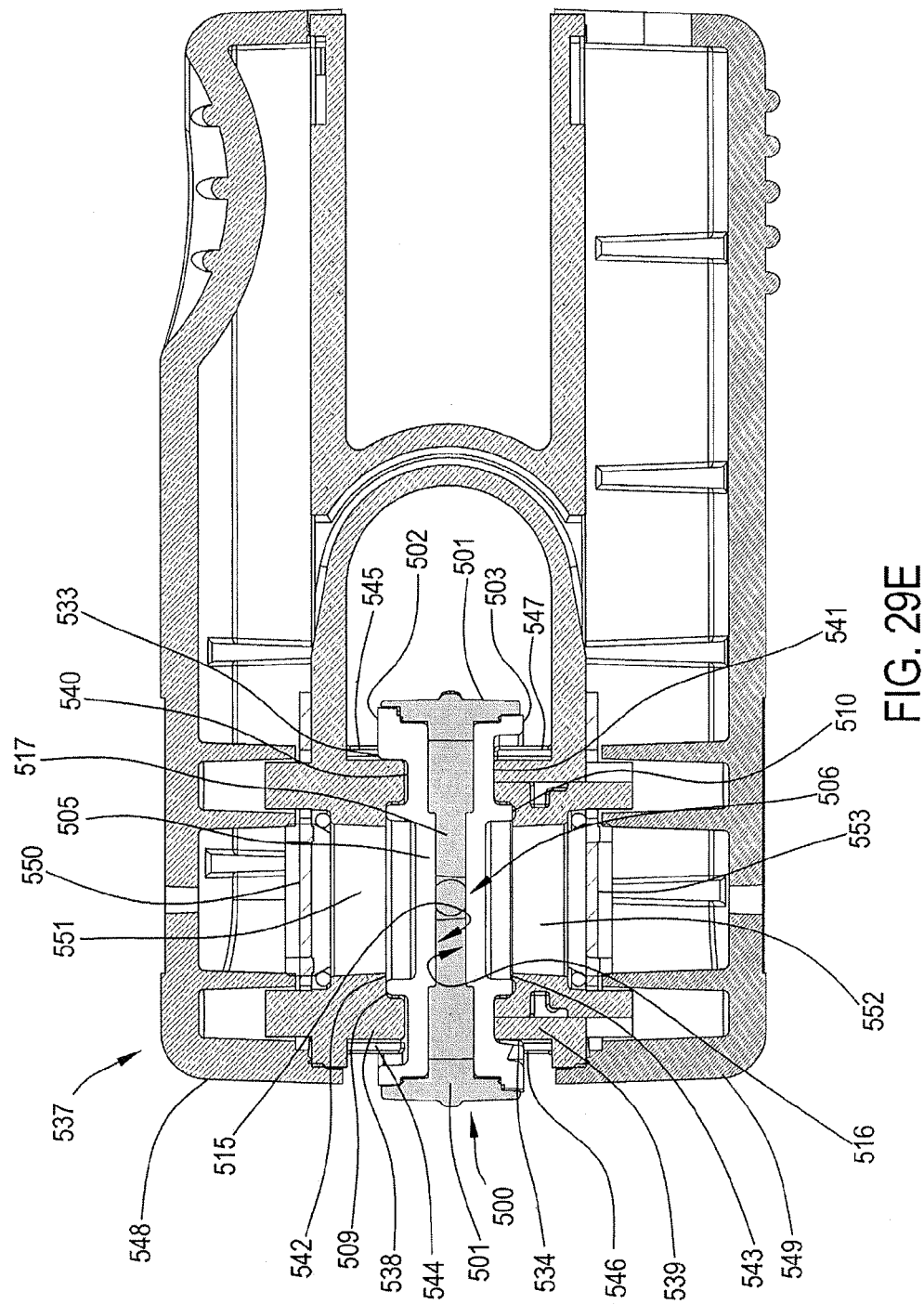
FIG. 29E is a transverse cross-sectional view of the blood chamber of FIGS. 25A-E when attached to the sensor clip assembly of FIG. 29A.

FIGS. 29D and 29E show, respectively, longitudinal and transverse cross-sectional views of blood chamber 500 when attached to sensor clip assembly 537. As shown, blood chamber 500 includes viewing windows 505, 506, which are bounded by annular walls 509, 510 of lenses 502, 503. While viewing windows 505, 506 should be made of clear material, it is desirable to tint main body portion 501 of blood chamber 500 in keeping with the first, second, and third embodiments described above in order to provide additional protection from unwanted light. Specifically, blue-tinted polycarbonate material may be used to manufacture main body portion 501.

When not attached to sensor clip assembly 537, the exterior sides of viewing windows 505, 506 are exposed on the exterior sides of blood chamber 500 (see FIGS. 25A-D). Blood chamber 500 includes inlet 524 and outlet 525 that are designed to be compatible with standard medical industry connecting devices conventionally known as luer lock connectors. In the illustrated embodiment, inlet 524 is integrally molded with main body portion 501, whereas outlet 525 comprises a suitable off-the-shelf connector 504 bonded to main body portion 501 of blood chamber 500. Alternatively, tubing can be attached directly to main body portion 501 of blood chamber 500 in place of connector 504.

In operation, blood flows from inlet 524 into blood flow cavity 517 of blood chamber 500. Blood flow cavity 517 provides a substantially flat, thin (e.g., less than 0.1 inches) viewing area for the blood flowing through blood chamber 500. While in blood flow cavity 517, multiplexed visible or infrared light at various wavelengths is transmitted through the blood flowing through the flat viewing area, and also through viewing windows 505, 506.

Attached to blood chamber 500 is sensor clip assembly 537. Sensor clip assembly 537 includes two arms, one comprising LED emitter subassembly 548, and the other comprising photodetector subassembly 549. LED emitter subassembly 548 contains emitter circuit board 550, which includes LEDs configured to emit radiation at the desired wavelengths, such as substantially 660 nm, 810 nm, and 1300 nm. The emitted radiation passes through molded diffusing lens 551. Photodetector subassembly 549 includes detector circuit board 553 that is configured to detect the radiation emitted by LED emitter subassembly 548. Detector circuit board 553 is mounted to receive the radiation emitted by LED emitter subassembly 548 through molded diffusing lens 552.

As shown in FIG. 29D, shroud 538 on LED emitter subassembly 548 extends beyond molded diffusing lens 551 and toward photodetector subassembly 549. Conversely, shroud 539 on photodetector subassembly 549 extends beyond molded diffusing lens 552 and toward LED emitter subassembly 548. Molding diffusing lenses 551, 552 are spaced apart from viewing windows 505, 506. When sensor clip assembly 537 is mated to blood chamber 500, shrouds 538, 539 are received on shroud mating surfaces 507, 508 of blood chamber 500 such that outer annular ledges 540, 541 of shrouds 538, 539 are substantially flush with shroud mating surfaces 507, 508. Furthermore, annular walls 509, 510, that bound viewing windows 505, 506, come into contact with inner annular ledges 542, 543 of shrouds 538, 539. In this manner, shrouds 538, 539 help to optically isolate the light emitted by LED emitter subassembly 548 and detected by photodetector subassembly 549.

The cross-sectional view of FIG. 29E shows anti-rotation tabs 533, 534, as well as receiving slots 544, 545 and 546, 547 of shrouds 538, 539. When the anti-rotation tabs of blood chamber 500 are received in the receiving slots of shrouds 538, 539, as shown in FIG. 29E, sensor clip assembly 537 is in a fixed predetermined positional and rotational orientation with respect to blood chamber 500.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Reference to the alignment of the photoemitters and the photodetectors concerns only an approximate relative physical alignment that enables light from the emitters to be received by the detectors. Except as indicated otherwise either expressly or in its context, references to "light" include electromagnetic radiation of any frequency and should not be construed as limited to radiation visible to the human eye. Unwanted light reaching the photodetectors is ambient light from sources other than the photoemitters and/or light from the photoemitters reaching the photodetectors indirectly such as through the light piping effect described above. Fastening and connecting as used herein is intended to include both mechanical engagements and pressure engagement. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A blood chamber for use in a system for monitoring extracorporeal blood flow, the blood chamber comprising:
    an inlet, an outlet and an internal blood flow cavity;
    a main body made of a material having an opaque color, the opaque color of the material being configured to attenuate ducting of light through the main body; and
    a clear first lens and a clear second lens, wherein the first and second lenses are constructed as mirror images of one another, and wherein the first lens is disposed in a recess on the first side of the main body and the second lens is disposed to a second recess on the second side of the main body;
    wherein the internal blood flow cavity is disposed within a space within the main body between the first and second lenses;
    wherein the blood chamber further comprises:
    an anti-rotation tab for preventing rotation of a sensor clip assembly attached to the blood chamber relative to the blood chamber, wherein the anti-rotation tab extends inwardly from a peripheral wall of at least one of the first and second lenses.

2. The blood chamber according to claim 1, wherein the first and second lenses comprise polycarbonate material.

3. The blood chamber according to claim 1, wherein the first and second lenses each include at least two turbulence posts disposed within the internal blood flow cavity, configured to suppress laminar blood flow in the internal blood flow cavity.

4. The blood chamber according to claim 1, wherein the main body comprises a receiving ledge for receiving each of the first and second lenses, and a protrusion for orienting a respective lens relative to the main body.

5. The blood chamber according to claim 1, wherein the first and second lenses further comprise:
    first and second viewing windows, the first viewing window being a part of the first lens and the second viewing window being a part of the second lens; and
    first and second shroud mating surfaces, the first shroud mating surface being a part of the first lens and the second shroud mating surface being a part of the second lens, the first and second shroud-mating surfaces being configured to cooperate with shrouds on a sensor clip assembly to shield extracorporeal blood flow in the internal blood flow cavity from external illumination.

6. The blood chamber according to claim 1, wherein the material of the main body is a polycarbonate material that is opaque to at least illumination of a first wavelength.

7. The blood chamber according to claim 5, wherein the first and second shroud mating surfaces are configured as annular wells of the first and second lenses, and the first and second shroud mating surfaces are separated from the first and second viewing windows by annular walls of the first and second lenses.

8. The blood chamber according to claim 6, wherein the main body comprises blue-tinted polycarbonate material.

9. A system for monitoring extracorporeal blood flow, the system comprising:
- a blood chamber comprising:
  - an inlet, an outlet and an internal blood flow cavity;
  - a main body made of a material having an opaque color, the opaque color of the material being configured to attenuate ducting of light through the main body; and
  - a first lens and a second lens, wherein the first and second lenses are constructed as mirror images of one another, and wherein the first lens is disposed in a first recess of the main body and the second lens is disposed in a second recess of the main body;
  - wherein the internal blood flow cavity is disposed within a space within the main body between the first and second lenses; and
- a sensor clip assembly, comprising two opposing arms configured to be mated to the blood chamber so as to attach the sensor clip assembly to the blood chamber;
- wherein the system further comprises an anti-rotation tab and an anti-rotation slot for preventing rotation of the sensor clip assembly relative to the blood chamber while the sensor clip assembly is attached to the blood chamber, wherein the anti-rotation tab extends inwardly from a peripheral wall of at least one of the first and second lenses, and wherein the anti-rotation slot corresponds to the anti-rotation tab and is disposed on at least one of the two opposing arms of the sensor clip assembly.

10. The system according to claim 9, wherein the first and second lenses comprise clear, polycarbonate material.

11. The system according to claim 9, wherein the first and second lenses each include at least two turbulence posts disposed within the internal blood flow cavity, configured to suppress laminar blood flow in the internal blood flow cavity.

12. The system according to claim 9, wherein the main body comprises a receiving ledge for receiving each of the first and second lenses, and a protrusion for orienting a respective lens relative to the main body.

13. The system according to claim 9, wherein the first and second lenses further comprise:
- first and second viewing windows, the first viewing window being a part of the first lens and the second viewing window being a part of the second lens; and
- first and second shroud mating surfaces, the first shroud mating surface being a part of the first lens and the second shroud mating surface being a part of the second lens; and
- wherein the two opposing arms each comprise a shroud, configured to be cooperate with a respective shroud-mating surface of each of the first and second lenses to shield extracorporeal blood flow in the internal blood flow cavity from external illumination.

14. The system according to claim 9, wherein the material of the main body is a polycarbonate material that is opaque to at least illumination of a first wavelength.

15. The system according to claim 13, wherein the first and second shroud mating surfaces are configured as annular wells of the first and second lenses;
- wherein the shrouds of the two opposing arms are configured to mate with the respective annular wells of the first and second lenses; and
- wherein the first and second shroud mating surfaces are separated from the first and second viewing windows by annular walls of the first and second lenses.

16. The system according to claim 14, wherein the main body comprises blue-tinted polycarbonate material.

* * * * *